(12) United States Patent
Kondo

(10) Patent No.: US 10,815,190 B2
(45) Date of Patent: Oct. 27, 2020

(54) QUATERNARY AMMONIUM COMPOUND, AND AGENT FOR SUPPRESSION OF GENERATION OF VOLATILE ORGANIC COMPOUND FROM POLYACETAL BY USE OF THE SAME

(71) Applicant: ASAHI KASEI KABUSHIKI KAISHA, Tokyo (JP)

(72) Inventor: Tomohiro Kondo, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 48 days.

(21) Appl. No.: 16/321,211

(22) PCT Filed: Jul. 28, 2017

(86) PCT No.: PCT/JP2017/027434
§ 371 (c)(1),
(2) Date: Jan. 28, 2019

(87) PCT Pub. No.: WO2018/021526
PCT Pub. Date: Feb. 1, 2018

(65) Prior Publication Data
US 2019/0161433 A1    May 30, 2019

(30) Foreign Application Priority Data

Jul. 29, 2016 (JP) .................. 2016-150397
Aug. 1, 2016 (JP) .................. 2016-150950
Jun. 9, 2017 (JP) .................. 2017-114287

(51) Int. Cl.
| | |
|---|---|
| C07C 217/08 | (2006.01) |
| C08G 2/30 | (2006.01) |
| C07C 53/06 | (2006.01) |
| C07C 53/10 | (2006.01) |
| C07C 53/122 | (2006.01) |
| C08L 59/00 | (2006.01) |
| C08K 5/17 | (2006.01) |
| C07C 229/76 | (2006.01) |
| C08K 5/19 | (2006.01) |

(52) U.S. Cl.
CPC ............ C07C 217/08 (2013.01); C07C 53/06 (2013.01); C07C 53/10 (2013.01); C07C 53/122 (2013.01); C07C 229/76 (2013.01); C08G 2/30 (2013.01); C08K 5/17 (2013.01); C08L 59/00 (2013.01); C08K 5/19 (2013.01)

(58) Field of Classification Search
USPC .................. 525/397, 398, 452, 472
See application file for complete search history.

(56) References Cited

U.S. PATENT DOCUMENTS

| | | |
|---|---|---|
| 3,337,504 A | 8/1967 | Fisher |
| 3,418,280 A | 12/1968 | Orgen |
| 4,366,305 A | 12/1982 | Amemiya et al. |
| 4,729,941 A | 8/1988 | Itoh et al. |
| 6,365,655 B1 | 4/2002 | Tanimura et al. |
| 2008/0200639 A1 | 8/2008 | Harashina et al. |

FOREIGN PATENT DOCUMENTS

| | | |
|---|---|---|
| DE | 22 39 592 A1 | 3/1973 |
| DE | 10 2006 050101 A1 | 7/2007 |
| EP | 0088541 A | 9/1983 |
| EP | 0 177 905 A2 | 4/1986 |
| EP | 1 881 018 A1 | 1/2008 |
| GB | 1404804 A | 3/1975 |
| JP | S39-008071 B | 5/1964 |
| JP | S40-010435 B | 5/1965 |
| JP | S40-011627 B | 6/1965 |
| JP | S43-001875 B | 1/1968 |
| JP | S43-007553 B | 3/1968 |
| JP | S44-011907 B | 5/1969 |
| JP | S48-079296 A | 10/1973 |
| JP | S57-117520 A | 7/1982 |
| JP | S58-011450 B | 3/1983 |
| JP | 58-152012 A | 9/1983 |
| JP | S62-129311 A | 6/1987 |
| JP | S62-251745 A | 11/1987 |

(Continued)

OTHER PUBLICATIONS

ESR for EP App. No. 17 834 528.6 dated Jul. 29, 2019.

(Continued)

Primary Examiner — Terressa Boykin
(74) Attorney, Agent, or Firm — Greenblum & Bernstein, P.L.C.

(57) ABSTRACT

A quaternary ammonium compound represented by the following formula (1):

$$[(R1)_m(R2)_{4-m}N^+]_n X^{n-} \quad (1)$$

wherein each R1 independently represents an unsubstituted alkyl group or substituted alkyl group having 1 to 30 carbon atoms; an aryl group having 6 to 20 carbon atoms; an aralkyl group where an unsubstituted alkyl group or substituted alkyl group having 1 to 30 carbon atoms is substituted with at least one aryl group having 6 to 20 carbon atoms; or an alkylaryl group where an aryl group having 6 to 20 carbon atoms is substituted with at least one unsubstituted alkyl group or substituted alkyl group having 1 to 30 carbon atoms;

each R2 independently represents a group having 2 to 60 carbon atoms and 2 to 30 oxygen atoms, the group represented by the following formula:

—(RO)k-H, wherein R represents a substituted or unsubstituted alkyl group and k represents a natural number of 2 or more.

6 Claims, No Drawings

(56) References Cited

FOREIGN PATENT DOCUMENTS

| | | |
|---|---|---|
| JP | H02-258748 A | 10/1990 |
| JP | H11-214373 A | 8/1999 |
| JP | H11-246736 A | 9/1999 |
| JP | 2000-128587 A | 5/2000 |
| JP | 2000-159850 A | 6/2000 |
| JP | 3087912 B | 7/2000 |
| JP | 2000-336241 A | 12/2000 |
| JP | 2000-351887 A | 12/2000 |
| JP | 2001-226558 A | 8/2001 |
| JP | 2004-262897 A | 9/2004 |
| JP | 2006-282836 A | 10/2006 |
| JP | 5031196 B | 7/2012 |
| JP | 2013-170176 A | 9/2013 |
| TW | 200640974 A | 3/1995 |
| WO | WO 2014/144341 A1 | 9/2014 |

OTHER PUBLICATIONS

Cannon et al., "Open-Chain Analogs of Muscarine Derivatives", Journal of Pharmaceutical Sciences 62(5):830-831 (1973).
Rose et al., "Phosphonium Polymethacrylates for Short Interfering RNA Delivery: Effect of Polymer and RNA Structural Parameters on Polyplex Assembly and Gene Knockdown", Biomarcomolecules 16(11):3480-3490 (2015).
Database CAPLUS Chemical Abstract XP-002792813 of JP H11-214373 A (Aug. 6, 1999), retrieved from STN Database accession No. 1999:490490.
Zhao et al., "Designing enzyme-compatible ionic liquids that can dissolve carbohydrates", Green Chemistry, vol. 10, 2008, pp. 696-705.
Pernak et al., "2,4-D based herbicidal ionic liquids", Tetrahedron, vol. 68, 2012, pp. 4267-4273.
ISR for PCT/JP2017/027434, dated Sep. 19, 2017.
IPRP/Written Opinion for PCT/JP2017/027434, dated Jan. 29, 2019.

QUATERNARY AMMONIUM COMPOUND, AND AGENT FOR SUPPRESSION OF GENERATION OF VOLATILE ORGANIC COMPOUND FROM POLYACETAL BY USE OF THE SAME

TECHNICAL FIELD

The present invention relates to a novel quaternary ammonium compound, and particularly relates to a quaternary ammonium compound suitable for use as an agent for suppression of generation of a volatile organic compound from polyacetal.

BACKGROUND ART

Polyacetal has balanced mechanical properties and excellent fatigue properties, and therefore is widely used in parts for automobiles, electronic equipment, electrical equipment, and the like. A polyacetal copolymer is produced by copolymerizing formaldehyde or a cyclic trimer thereof, which is a cyclic acetal such as trioxane, with any one of a cyclic ether and a cyclic formal, or both thereof. A polyacetal copolymer obtained by such copolymerization, however, bears a —(OCH2)n-OH group at some of molecular terminals, and cannot be put into practical use as it is because such a terminal group is thermally unstable and thus is easily decomposed by heating or the like during a molding process, to cause generation of a large amount of formaldehyde. That is, generation of a large amount of formaldehyde causes disadvantages such as foaming of a resin in molding and a poor appearance due to lines which are caused by outgassing of formaldehyde and which remain on the surface of a molded article. Furthermore, formaldehyde generated is oxidized to formic acid due to oxygen present in a molding machine, thereby promoting decomposition of a main chain of the polyacetal copolymer.

In particular, in recent years, a material having an extremely small amount of formaldehyde generated from a product obtained by molding has been demanded from the viewpoint that formaldehyde is a substance undesirable for the human body, and a polyacetal having a small amount of formaldehyde generated has been invented.

In recent years, a material suppressed in the amount of formaldehyde generated, to a much lower extent than conventional one, has been demanded in the fields with extremely severe demands, for example, in applications where such a material is also brought into contact with the inside of the body of organisms. In addition, it has been increasingly demanded to decrease not only formaldehyde, but also acetaldehyde and furthermore acrolein highly toxic to microorganisms. Accordingly, a material having the extremely small amounts of not only above stated formaldehyde generated, but also acetaldehyde and acrolein generated is much needed.

Since polyacetal is generally low in stability to heat or the like, polyacetal is generally used in the form of a resin composition to which a heat stabilizer or the like is added. It is essential that the amount of formaldehyde generated from polyacetal itself serving as a base resin be small in order to provide a material having an extremely small amount of formaldehyde generated.

Polyacetal bears an unstable terminal portion after polymerization, thereby generating formaldehyde. As a method for stabilizing a polyacetal copolymer (hereinafter, sometimes referred to as "crude polyacetal".), a method where a terminal is acetylated, etherified or urethanated, a method where the unstable terminal portion is decomposed, and the like are known.

Among them, the method for stabilizing by decomposing the unstable terminal portion is effective. As the method for stabilizing by decomposing the unstable terminal portion, a method for heating and stabilizing a crude polyacetal copolymer in water or an organic solvent in the presence of a basic substance which can decompose the unstable terminal portion, a method for stabilizing a crude polyacetal copolymer in a heated and molten state, and the like are known. While the method for heating and stabilizing a crude polyacetal copolymer in water or an organic solvent requires operations such as separation (filtration), recovery, and washing, the method for stabilizing in a heated and molten state is an industrially most effective method because a polyacetal copolymer stabilized is directly obtained.

A conventionally known heating treatment method is a method where a crude polyacetal copolymer is subjected to a heating treatment for removal of an unstable terminal portion, with being kept in a heterogeneous system in a medium (for example, water or a water/methanol mixed liquid) in which no polyacetal copolymer can be dissolved (for example, Patent Literature 1 and Patent Literature 2). The method, however, not only is needed to be operated at a temperature near the melting point of the polyacetal copolymer in order to increase the decomposition rate of the unstable terminal portion, but also is needed to be performed as a long-term treatment in order to decrease the unstable terminal portion. The resulting polyacetal copolymer is not sufficient in decomposition and removal of the unstable terminal portion even if such a treatment is performed, and a problem is also that the polyacetal copolymer is easily colored due to a treatment at a high temperature for a long time.

Patent Literature 3 discloses a method for removing an unstable terminal portion by exposing a crude polyacetal copolymer into a saturated vapor mixture made of a volatile organic solvent, a volatile base and water under a pressure equal to or higher than the atmospheric pressure at a temperature equal to or higher than 100° C. The method, however, is also not sufficient in removal of the unstable terminal portion. A method is also known where an unstable terminal portion is also known.

For example, Patent Literature 4 proposes a method where a molten copolymer is kneaded on a roll mill for a certain time, Patent Literature 5 or Patent Literature 6 proposes a method where a heating and melting treatment is performed using an extruder or the like in the presence of water, an alcohol or the like, or furthermore an alkaline component, Patent Literature 7 proposes a method where a crude polyacetal copolymer is heated and molten, and thereafter an unstable portion is decomposed and removed by use of a special surface renewal mixer under reduced pressure, Patent Literature 8 proposes a method where an unstable portion is decomposed in a reaction apparatus configured from a single-screw extruder for melting a crude polyacetal copolymer, a static mixer having a reaction zone for decomposition of an unstable portion with mixing of the crude polyacetal copolymer with a reactant including water and a compound which generates a hydroxide in the presence of water, in accordance with the principle of flow division and rearrangement, and a vent type screw extruder for removal of a volatile content, which is arranged immediately after the static mixer, and Patent Literature 9 proposes a method where a powdered or powdered crude polyacetal copolymer is treated under reduced pressure at a temperature lower than the melting temperature by 5 to 35° C., and thereafter subjected to a heating and melting treatment with an extruder, respectively.

Such a method where only a thermally unstable terminal portion is decomposed and removed with a crude polyacetal copolymer being kept in a molten state by heating can allow significant stabilization and a polyacetal copolymer subjected to such a treatment can be put in practical use, but a thermally unstable terminal portion still remains and may cause an undesirable phenomenon, for example, the occurrence of a mold deposit in a molding process or the like, and it is thus strongly demanded to provide a much more stable polymer.

In these known methods, in order to increase decomposition rate, it has been necessary to add, to a polyacetal copolymer, the compound or the like (for example, amines generally used for such applications) which generates a hydroxide in the presence of the basic substance, an alkaline component, or water, and to increase the amount of such a compound added. If, however, the amount of the amines or the like added is excessively increased, the polymer is colored. Furthermore, in order to decrease an unstable terminal portion, it has been necessary to perform a treatment for a long period or to perform a treatment multiple times. Thus, not only a polyacetal copolymer stabilized is colored and degraded, but also increases in size and complexity of an apparatus are caused. Furthermore, a problem is also that decomposition and removal of an unstable terminal portion of a crude polyacetal copolymer are not sufficient.

In order to solve these problems, Patent Literature 10 discloses, as a stabilization method for providing a polyacetal copolymer having a very small amount of an unstable terminal portion in a simple manner, a method where a heat treatment is performed in the presence of a quaternary ammonium compound having a specified structure. This method, while is considered to be able to realize exponential stabilization of a thermally unstable terminal portion of a polyacetal copolymer and solve various problems about the above stabilization method, does not lead to any suppression of generation of acetaldehyde and acrolein generated after heating and melting in molding or the like.

Furthermore, Patent Literature 11 discloses, as a method for improving odor properties with removing an unstable terminal, a stabilization method mainly using a quaternary ammonium compound of polyacrylic acid. This method, however, does not lead to odor evaluation at a substantial processing temperature, and there remains a problem in terms of odor evaluation at a temperature equal to or higher than the processing temperature. In addition, polyacrylic acid has a high boiling point and remains in a polymer, and therefore cannot be said to have no concerns about not only a decomposition behavior in heating, but also colorability, and this method does not lead to any suppression of generation of acetaldehyde and acrolein generated after heating and melting in molding or the like.

CITATION LIST

Patent Literature

Patent Literature 1: Japanese Patent Publication No. 40-10435
Patent Literature 2: Japanese Patent Publication No. 43-7553
Patent Literature 3: Japanese Patent Publication No. 40-11627
Patent Literature 4: Japanese Patent Publication No. 39-8071
Patent Literature 5: Japanese Patent Publication No. 43-1875 (corresponding to U.S. Pat. No. 3,337,504)
Patent Literature 6: Japanese Patent Publication No. 44-11907 (corresponding to U.S. Pat. No. 3,418,280)
Patent Literature 7: Japanese Patent Publication No. 58-11450 (corresponding to U.S. Pat. No. 4,366,305)
Patent Literature 8: Japanese Patent Laid-Open No. 58-152012 (corresponding to European Patent No. 88,541)
Patent Literature 9: Japanese Patent Laid-Open No. 62-129311
Patent Literature 10: Japanese Patent No. 3087912
Patent Literature 11: Japanese Patent No. 5031196

SUMMARY OF INVENTION

Technical Problem

An object of the present invention is then to provide a polyacetal resin composition favorable in color tone, causing less generation of formaldehyde, acetaldehyde and acrolein even when subjected to a heating treatment such as heating and melting, further having a small amount of a mold deposit in molding, and high in purity.

Solution to Problem

The present inventors have intensive studies in order to solve the problems, and as a result, have found that a novel quaternary ammonium compound having a specified structure has an effect on suppression of generation of a volatile organic substance from polyacetal subjected to a heating treatment such as heating and melting, thereby leading to completion of the present invention.

The present inventors further have found that when the quaternary ammonium compound having a specified structure coexists with a (poly)alkylene glycol having a specified structure, the degradation thereof over time can be prevented, and even when stored for a long period, not only a polyacetal favorable in color tone can be produced, but also the effect of suppression of generation of a volatile organic substance from polyacetal after a heating treatment is not deteriorated.

The present invention is as follows.

[1]

A quaternary ammonium compound represented by the following formula (1):

$$[(R1)_m(R2)_{4-m}N^+]_n X^{n-} \qquad (1)$$

wherein each R1 independently represents an unsubstituted alkyl group or substituted alkyl group having 1 to 30 carbon atoms; an aryl group having 6 to 20 carbon atoms; an aralkyl group where an unsubstituted alkyl group or substituted alkyl group having 1 to 30 carbon atoms is substituted with at least one aryl group having 6 to 20 carbon atoms; or an alkylaryl group where an aryl group having 6 to 20 carbon atoms is substituted with at least one unsubstituted alkyl group or substituted alkyl group having 1 to 30 carbon atoms; wherein the unsubstituted alkyl group and the substituted alkyl group are straight, branched, or cyclic; the substituent of the substituted alkyl group is halogen, a hydroxyl group, an aldehyde group, a carboxyl group, an amino group, or an amide group; and any hydrogen atom in the unsubstituted alkyl group, aryl group, aralkyl group, and alkylaryl group may be replaced by halogen;

each R2 independently represents a group having 2 to 60 carbon atoms and 2 to 30 oxygen atoms, the group represented by the following formula:

—(RO)k-H, wherein R represents a substituted or unsubstituted alkyl group and k represents a natural number of 2 or more;

m and n each represent an integer of 1 to 3; and

X represents a hydroxyl group, or an acid residue of a compound selected from the group consisting of a monocarboxylic acid having 1 to 20 carbon atoms, a hydroacid, an oxo-acid, an inorganic thioacid, and an organic thioacid having 1 to 20 carbon atoms, the acid residue being a group including no nitrogen atom.

[2]

The quaternary ammonium compound according to [1], wherein X in the formula (1) represents an acid residue of a monocarboxylic acid.

[3]

The quaternary ammonium compound according to [2], wherein the monocarboxylic acid is formic acid, acetic acid, or propionic acid.

[4]

The quaternary ammonium compound according to any of [1] to [3], wherein R2 in the formula (1) has 2 to 6 carbon atoms.

[5]

A quaternary ammonium composition comprising:

the quaternary ammonium compound (A) according to any of [1] to [4]; and a (poly)alkylene glycol (B) represented by the following formula (2), and/or a quaternary ammonium compound (C) represented by the following formula (3):

R3-O—(C$_2$H$_4$O)$_p$—R4    (2)

wherein R3 and R4 each independently represent a hydrogen atom; an unsubstituted alkyl group or substituted alkyl group having 1 to 30 carbon atoms; an aryl group having 6 to 20 carbon atoms; an aralkyl group where an unsubstituted alkyl group or substituted alkyl group having 1 to 30 carbon atoms is substituted with at least one aryl group having 6 to 20 carbon atoms; or an alkylaryl group where an aryl group having 6 to 20 carbon atoms is substituted with at least one unsubstituted alkyl group or substituted alkyl group having 1 to 30 carbon atoms; wherein the unsubstituted alkyl group or substituted alkyl group is straight, branched, or cyclic; the substituent of the substituted alkyl group is halogen, a hydroxyl group, an aldehyde group, a carboxyl group, an amino group, or an amide group; and any hydrogen atom in the unsubstituted alkyl group, aryl group, aralkyl group, and alkylaryl group may be replaced by halogen; and p represents a natural number;

[R5R6R7R8N$^+$]$_l$Y$^{l-}$    (3)

wherein R5, R6, R7, and R8 each independently represent an unsubstituted alkyl group or substituted alkyl group having 1 to 30 carbon atoms; an aryl group having 6 to 20 carbon atoms; an aralkyl group where an unsubstituted alkyl group or substituted alkyl group having 1 to 30 carbon atoms is substituted with at least one aryl group having 6 to 20 carbon atoms; or an alkylaryl group where an aryl group having 6 to 20 carbon atoms is substituted with at least one unsubstituted alkyl group or substituted alkyl group having 1 to 30 carbon atoms; wherein the unsubstituted alkyl group and the substituted alkyl group are straight, branched, or cyclic; the substituent of the substituted alkyl group is halogen, a hydroxyl group, an aldehyde group, a carboxyl group, an amino group, or an amide group; and any hydrogen atom in the unsubstituted alkyl group, aryl group, aralkyl group, and alkylaryl group may be replaced by halogen;

l represents an integer of 1 to 3; and

Y represents a hydroxyl group, or an acid residue of a compound selected from the group consisting of a carboxylic acid having 1 to 20 carbon atoms, a hydroacid, an oxo-acid, an inorganic thioacid, and an organic thioacid having 1 to 20 carbon atoms.

[6]

The quaternary ammonium composition according to [5], further comprising at least one metal atom selected from the group consisting of magnesium, sodium, and calcium.

[7]

An agent for suppression of generation of a volatile organic compound from polyacetal, the agent comprising the quaternary ammonium compound according to any of [1] to [4] or the quaternary ammonium composition according to [5] or [6].

[8]

A polyacetal resin composition comprising: polyacetal; and the agent for suppression of generation of a volatile organic compound from polyacetal according to [7].

[9]

The polyacetal resin composition according to [8], wherein a concentration n of nitrogen derived from the quaternary ammonium compound (A) represented by the formula (I), represented by the following expression, is 0.1 ppb or more and 30 ppm or less on a mass basis:

$n = S \times 14 / T$    (I)

wherein S represents an amount of the quaternary ammonium compound (A) based on a total amount of polyacetal and the quaternary ammonium compound (A), 14 represents an atomic weight of nitrogen, and T represents a molecular weight of the quaternary ammonium compound (A).

[10]

A method for producing polyacetal, comprising:

a step of subjecting a polyacetal having a thermally unstable terminal portion to a heat treatment in the presence of the quaternary ammonium compound according to any of [1] to [4] or the quaternary ammonium composition according to [5] or [6].

Advantageous Effects of Invention

Using the quaternary ammonium compound of the present invention can provide a polyacetal favorable in color tone and causing less generation of formaldehyde, acetaldehyde, and acrolein, and can further provide a polyacetal resin composition having a small amount of a mold deposit in molding.

Furthermore, the quaternary ammonium composition of the present invention does not cause such effects to be deteriorated even in storage for a long period.

DESCRIPTION OF EMBODIMENTS

Hereinafter, an embodiment for carrying out the present invention (hereinafter, referred to as "the present embodiment".) will be described in detail. The present invention is not intended to be limited to the following embodiment, and can be variously modified and carried out within the gist thereof.

1. Quaternary Ammonium Compound

First, a novel quaternary ammonium compound (A) represented by formula (1) in the present embodiment will be described.

The quaternary ammonium compound (A) of the present embodiment is represented by the following formula (1):

$$[(R1)_m(R2)_{4-m}N^+]_n X^{n-} \quad (1)$$

wherein each R1 independently represents an unsubstituted alkyl group or substituted alkyl group having 1 to 30 carbon atoms; an aryl group having 6 to 20 carbon atoms; an aralkyl group where an unsubstituted alkyl group or substituted alkyl group having 1 to 30 carbon atoms is substituted with at least one aryl group having 6 to 20 carbon atoms; or an alkylaryl group where an aryl group having 6 to 20 carbon atoms is substituted with at least one unsubstituted alkyl group or substituted alkyl group having 1 to 30 carbon atoms; wherein the unsubstituted alkyl group or substituted alkyl group is straight, branched, or cyclic; the substituent of the substituted alkyl group is halogen, a hydroxyl group, an aldehyde group, a carboxyl group, an amino group, or an amide group; and any hydrogen atom in the unsubstituted alkyl group, aryl group, aralkyl group, and alkylaryl group may be replaced by halogen;

each R2 independently represents a group having 2 to 60 carbon atoms and 2 to 30 oxygen atoms, the group represented by the following formula:

—(RO)k-H, wherein R represents a substituted or unsubstituted alkyl group and k represents a natural number of 2 or more; and m and n each represent an integer of 1 to 3. A higher n value can more highly cause a side reaction, and it is thus particularly preferable that n represent 1 and m represent 3 in order to obtain those with a high purity and furthermore from the viewpoint of availability.

X represents a hydroxyl group, or an acid residue of a compound selected from the group consisting of a monocarboxylic acid having 1 to 20 carbon atoms, a hydroacid, an oxo-acid, an inorganic thioacid, and an organic thioacid having 1 to 20 carbon atoms, the acid residue being a group including no nitrogen atom.

If X represents a group including a nitrogen atom, suppression of generation of acetaldehyde and acrolein in heating is not effectively achieved.

In the formula (1), R1 is preferably an alkyl group having 1 to 5 carbon atoms or a hydroxyalkyl group having 2 to 4 carbon atoms from the viewpoints of availability and ease of production.

In the formula (1), R2 is preferably a group having 2 to 60 carbon atoms and 2 to 30 oxygen atoms and represented by the following formula:

—(RO)k-H, wherein R represents a substituted or unsubstituted alkyl group and k represents a natural number of 2 or more.

Selecting such a group as R2 allow suppressing generation of formaldehyde, acetaldehyde and acrolein from polyacetal when high-temperature heating such as heating and melting is performed.

If R2 has more than 60 carbon atoms or more than 30 oxygen atoms, isolation and production of the quaternary ammonium compound may require time.

It is preferable from the viewpoint of synthesis of the quaternary ammonium compound that R2 has 2 to 10 carbon atoms and 2 to 5 oxygen atoms, and it is more preferable from the viewpoint of colorability after melting and heating that R2 has 2 to 6 carbon atoms and 2 to 3 oxygen atoms.

In the formula (1), X is preferably an acid residue of a monocarboxylic acid from the viewpoint of availability. In particular, X is preferably an acid residue of at least one selected from the group consisting of formic acid, acetic acid, and propionic acid from the viewpoint of ease of handling.

Specific examples of the quaternary ammonium compound (A) of the present embodiment include hydroxides such as 1-hydroxymethoxy-N-((hydroxymethoxy)methyl)-N,N-dimethylmethaneammonium, 2-(2-hydroxyethoxy)-N-(2-(2-hydroxyethoxy)ethyl)-N,N-dimethylethane-1-ammonium, N-ethyl-N,N-bis((hydroxymethoxy)methyl)ethane ammonium, 2-(2-hydroxyethoxy)-N-(2-(2-hydroxyethoxy)ethyl)-N,N-dimethylethane-1-ammonium, N,N,N-triethyl-2-(2-(2-hydroxy)ethoxy)ethane-1-ammonium, N-(2-(2-(hydroxymethoxy)ethoxy)ethyl)-N,N-dipropylpropane-1-ammonium, N-((hydroxymethoxy)methoxy)methyl)-N,N-dipropylpropane-1-ammonium, and N-(2-(2-(2-hydroxyethoxy)ethoxy)ethyl)-N,N-dipropylpropane-1-ammonium; salts of hydroacids such as hydrochloric acid, hydrobromic acid, and hydrofluoric acid; salts of oxo-acids such as sulfuric acid, nitric acid, phosphoric acid, carbonic acid, boric acid, chloric acid, iodic acid, silicic acid, perchloric acid, chlorous acid, hypochlorous acid, chlorosulfuric acid, amidosulfuric acid, disulfuric acid, and tripolyphosphoric acid; salts of thioacids such as thiosulfuric acid; and salts of monocarboxylic acids such as formic acid, acetic acid, propionic acid, butanoic acid, isobutyric acid, pentanoic acid, caproic acid, caprylic acid, capric acid, and benzoic acid.

Hydroxides, among them, are strongly alkaline and therefore are needed to be carefully handled. Therefore, the form of any salt is preferably used, and a monocarboxylic acid salt is particularly preferable.

2. Quaternary Ammonium Composition

Next, a quaternary ammonium composition of the present embodiment will be described.

The quaternary ammonium composition of the present embodiment contains not only the quaternary ammonium compound (A), but also a (poly)alkylene glycol (B) represented by formula (2) and/or a quaternary ammonium compound (C) represented by formula (3).

<(Poly)alkylene Glycol (B)>

In the present embodiment, the (poly)alkylene glycol (B) is represented by the following formula (2):

$$R3-(C_2H_4O)_p-R4 \quad (2)$$

wherein R3 and R4 each independently represent a hydrogen atom, an unsubstituted alkyl group or substituted alkyl group having 1 to 30 carbon atoms; an aryl group having 6 to 20 carbon atoms; an aralkyl group where an unsubstituted alkyl group or substituted alkyl group having 1 to 30 carbon atoms is substituted with at least one aryl group having 6 to 20 carbon atoms; or an alkylaryl group where an aryl group having 6 to 20 carbon atoms is substituted with at least one unsubstituted alkyl group or substituted alkyl group having 1 to 30 carbon atoms; wherein the unsubstituted alkyl group or substituted alkyl group is straight, branched, or cyclic; the substituent of the substituted alkyl group is halogen, a hydroxyl group, an aldehyde group, a carboxyl group, an amino group, or an amide group; any hydrogen atom in the unsubstituted alkyl group, aryl group, aralkyl group, and alkylaryl group may be replaced by halogen; and p represents a natural number.

In the present embodiment, by coexistence of the quaternary ammonium compound (A) and the (poly)alkylene glycol (B) coexist, uniform dispersion of the quaternary ammonium compound (A) in polyacetal can be promoted.

Furthermore, the (poly)alkylene glycol (B) is also effective for storage stability of the quaternary ammonium compound (A), and not only a polyacetal pellet excellent in color tone can be obtained even when the quaternary ammonium composition is used after long-term storage, but also a mold is maintained to have low contamination properties in repeated molding of the polyacetal pellet introduced into a molding machine. Furthermore, the effect of suppression of generation of a volatile organic substance from polyacetal after a heating treatment is also maintained.

The (poly)alkylene glycol (B) is preferably contained at a rate of 0.01% by mass to 80% by mass based on the amount of the quaternary ammonium compound (A), or based on the total amount of the compound (A) and a quaternary ammonium compound (C) described below when the compound (C) is contained. The content of the (poly)alkylene glycol (B) is preferably 1% by mass to 50% by mass, further preferably 3% by mass to 30% by mass from the viewpoint that a polyacetal excellent in heat stability and high in purity is obtained. On the other hand, an extremely high content of the (poly)alkylene glycol (B) may also cause a molded article to be colored, and therefore the content is preferably 80% by mass or less, more preferably 70% by mass or less from such a viewpoint.

The high-temperature heat stability of the (poly)alkylene glycol is generally superior when p is a smaller value, and therefore p in the formula (2) is preferably 1 to 10, more preferably 1 to 5, most preferably 1 to 3.

The substituents in R3 and R4 are each preferably a hydrogen atom or an alkyl group having 1 to 10 carbon atoms from the viewpoint of availability, and, in particular, preferably a hydrogen atom or an alkyl group having 1 to 5 carbon atoms, most preferably a hydrogen atom or an alkyl group having 1 to 3 carbon atoms from the viewpoint of ensuring the high-temperature heat stability of the (poly) alkylene glycol.

<Quaternary Ammonium Compound (C)>

The quaternary ammonium composition of the present embodiment may include not only the quaternary ammonium compound (A), but also a quaternary ammonium compound (C) represented by the following formula (3):

wherein R5, R6, R7, and R8 each independently represent an unsubstituted alkyl group or substituted alkyl group having 1 to 30 carbon atoms; an aryl group having 6 to 20 carbon atoms; an aralkyl group where an unsubstituted alkyl group or substituted alkyl group having 1 to 30 carbon atoms is substituted with at least one aryl group having 6 to 20 carbon atoms; or an alkylaryl group where an aryl group having 6 to 20 carbon atoms is substituted with at least one unsubstituted alkyl group or substituted alkyl group having 1 to 30 carbon atoms; wherein the unsubstituted alkyl group and the substituted alkyl group are straight, branched, or cyclic; the substituent of the substituted alkyl group is halogen, a hydroxyl group, an aldehyde group, a carboxyl group, an amino group, or an amide group; and any hydrogen atom in the unsubstituted alkyl group, aryl group, aralkyl group, and alkylaryl group may be replaced by halogen;

l represents an integer of 1 to 3; and

Y represents a hydroxyl group, or an acid residue of a compound selected from the group consisting of a carboxylic acid having 1 to 20 carbon atoms, a hydroacid, an oxo-acid, an inorganic thioacid, and an organic thioacid having 1 to 20 carbon atoms.

Examples of such a quaternary ammonium compound (C) include hydroxides such as tetramethylammonium, tetraethylammonium, tetrapropylammonium, tetra-n-butylammonium, cetyltrimethylammonium, tetradecyltrimethylammonium, 1,6-hexamethylenebis(trimethylammonium), decamethylene-bis-(trimethylammonium), trimethyl-3-chloro-2-hydroxypropylammonium, trimethyl(2-hydroxyethyl)ammonium, triethyl(2-hydroxyethyl)ammonium, tripropyl(2-hydroxyethyl)ammonium, tri-n-butyl(2-hydroxyethyl)ammonium, trimethylbenzylammonium, triethylbenzylammonium, tripropylbenzylammonium, tri-n-butylbenzylammonium, trimethylphenylammonium, triethylphenylammonium, trimethyl-2-oxyethylammonium, monomethyltrihydroxyethylammonium, monoethyltrihydroxyethylammonium, octadecyltri(2-hydroxyethyl)ammonium, and tetrakis(hydroxyethyl)ammonium; salts of hydroacids such as hydrochloric acid, hydrobromic acid, and hydrofluoric acid; salts of oxo-acids such as sulfuric acid, nitric acid, phosphoric acid, carbonic acid, boric acid, chloric acid, iodic acid, silicic acid, perchloric acid, chlorous acid, hypochlorous acid, chlorosulfuric acid, amidosulfuric acid, disulfuric acid, and tripolyphosphoric acid; salts of thioacids such as thiosulfuric acid; and salts of monocarboxylic acids such as formic acid, acetic acid, propionic acid, butanoic acid, isobutyric acid, pentanoic acid, caproic acid, caprylic acid, capric acid, benzoic acid, and oxalic acid. Hydroxides, among them, are strongly alkaline and therefore are needed to be carefully handled. Therefore, the form of any salt is preferably used, and a carboxylic acid salt is particularly preferable.

The quaternary ammonium compound (C) may be used singly or in combinations of two or more kinds thereof.

<Metal Atom>

The quaternary ammonium composition of the present embodiment preferably further includes a specific metal atom.

In the present embodiment, when the quaternary ammonium composition includes a specific metal atom, the effect of reducing the amount of acrolein from polyacetal after stabilization of an unstable terminal described below is performed by using the quaternary ammonium composition is enhanced. Examples of such a metal atom include magnesium, sodium, and calcium. Furthermore, including magnesium, sodium, or calcium can also suppress coloration in concentration of the quaternary ammonium composition.

The metal atom is preferably included in an amount of 0.001 ppm or more relative to the quaternary ammonium compound (A) (the total of the compound (A) and a quaternary ammonium compound (C) when the compound (C) is used in combination) included in the quaternary ammonium composition. It is understood that a common metal atom is high in boiling point and is hardly removed, and therefore the amount of the metal atom is preferably 10 ppm or less.

On the other hand, if the quaternary ammonium composition includes a potassium atom, coloration in concentration of the quaternary ammonium composition can be increased.

3. Agent for Generation of Volatile Organic Compound from Polyacetal

The quaternary ammonium compound (A) or the quaternary ammonium composition of the present embodiment can be each used as an agent for suppression of generation of a volatile organic compound from polyacetal.

The agent for suppression of generation of a volatile organic compound from polyacetal of the present embodiment includes the quaternary ammonium compound (A), and, if necessary, the (poly)alkylene glycol (B), the quaternary ammonium compound (C), and at least one metal atom selected from the group consisting of magnesium, sodium, and calcium, and can further contain a solvent and any additive.

The dosage form of the agent for suppression of generation of a volatile organic compound from polyacetal of the present embodiment is not limited, and may be, for example, a solid (powder), or may be a solution in which the quaternary ammonium composition is dissolved in any solvent (water or the like).

4. Polyacetal Resin Composition

Next, a polyacetal resin composition of the present embodiment will be described.

The polyacetal resin composition of the present embodiment includes an agent for generation of a volatile organic compound from polyacetal of the present embodiment, and polyacetal.

The polyacetal included in the polyacetal resin composition of the present embodiment is not limited, a polyacetal on which the quaternary ammonium compound (A) of the present embodiment (agent for generation of a volatile organic compound from polyacetal) effectively acts is a polymer having an oxymethylene group in a main chain, and representative examples thereof can include a polyacetal copolymer obtained by copolymerizing a formaldehyde monomer, or a cyclic oligomer of formaldehyde, such as a trimer (trioxane) or a tetramer (tetraoxane), with a cyclic ether or a cyclic formal, such as ethylene oxide, propylene oxide, epichlorohydrin or 1,3-dioxolane, or a cyclic formal of glycol or diglycol, such as 1,4-butanediol formal. A polyacetal copolymer having a branch, obtained by copolymerizing a monofunctional glycidyl ether, or a polyacetal copolymer having a crosslinked structure, obtained by copolymerizing a polyfunctional glycidyl ether can also be used. Furthermore, a compound having a functional group such as a hydroxyl group at both terminals or one terminal, such as a polyacetal homopolymer having a block component, obtained by polymerizing a formaldehyde monomer or a cyclic oligomer of formaldehyde in the presence of a polyalkylene glycol, or a similar compound having a functional group such as a hydroxyl group at both terminals or one terminal, such as a polyacetal copolymer having a block component, obtained by copolymerizing a formaldehyde monomer or a cyclic oligomer of formaldehyde, such as a trimer (trioxane) or a tetramer (tetraoxane), with a cyclic ether or a cyclic formal in the presence of a hydrogenated polybutadiene glycol can also be used.

As described above, the quaternary ammonium compound (A) of the present embodiment can be used in both the polyacetal homopolymer and copolymer.

Meanwhile, polyacetal generally includes a thermally unstable terminal portion (a group including a hydroxymethyl group, such as a —$CH_2OH$ group or a —$(OCH_2)_n$—OH group), and therefore may generate formaldehyde, and/or, in some cases, acetaldehyde and acrolein when heated. In the present embodiment, the quaternary ammonium compound (A) is utilized to decompose and remove an unstable terminal portion of polyacetal in heating, thereby suppressing generation of formaldehyde and the like. In particular, a polyacetal copolymer includes an unstable terminal portion in a large amount, and thus the quaternary ammonium compound (A) of the present embodiment can be effectively used for a polyacetal copolymer.

Hereinafter, a polyacetal copolymer will be described in detail.

The proportion of a comonomer such as 1,3-dioxolane in a polyacetal copolymer is generally 0.01 to 60% by mol, preferably 0.03 to 20% by mol, further preferably 0.05 to 15% by mol, most preferably 0.1 to 10% by mol based on 1 mol of such trioxane.

The polymerization catalyst used to provide a polyacetal copolymer by polymerization is not particularly limited, and a cationic active catalyst such as Lewis acid, protonic acid, and ester or anhydride thereof is preferable.

Examples of Lewis acid include halides of boric acid, tin, titanium, phosphorus, arsenicum, and antimony, and specific examples include boron trifluoride, tin tetrachloride, titanium tetrachloride, phosphorus pentafluoride, phosphorus tetrachloride, antimony pentafluoride, and complex compounds or salts thereof. Specific examples of protonic acid, and ester or anhydride thereof include perchloric acid, trifluoromethanesulfonic acid, perchloric acid-tertiary butyl ester, acetyl perchlorate, isopolyacids, heteropolyacids, and trimethyl oxonium hexafluorophosphate. Among them, boron trifluoride; boron trifluoride hydrate; and a coordinated complex compound of an organic compound including an oxygen atom or a sulfur atom, with boron trifluoride are preferable, and specific suitable examples can include boron trifluoride diethyl ether, and boron trifluoride di-n-butyl ether.

The polymerization method of a polyacetal copolymer is not particularly limited, and is generally performed by bulk polymerization and can be performed in any of a batch manner and a continuous manner.

For example, a self-cleaning type extrusion kneader such as a co-kneader, a twin-screw type continuous extrusion kneader, or a twin-paddle type continuous mixer can be used as a polymerization apparatus, and a monomer in a molten state is fed to a polymerization machine, to provide a polyacetal copolymer in the form of a solid mass along with the progression of polymerization.

The polyacetal having an unstable terminal group can allow generation of formaldehyde and the like due to a heating treatment to be reduced, in use in the form of a composition in which the quaternary ammonium compound (A) of the present embodiment coexists.

The concentration of the quaternary ammonium compound (A) in the polyacetal resin composition of the present embodiment is preferably 0.1 ppb or more and 30 ppm or less on a mass basis in terms of the concentration n of nitrogen derived from the quaternary ammonium compound (A), represented by the following expression (I).

Such a range enables generation of acrolein and acetaldehyde to be efficiently suppressed. When the concentration is 0.1 ppb or more, generation of acrolein can be effectively suppressed, and when the concentration is 30 ppm or less, generation of acetaldehyde, and yellowing of a polyacetal resin can be effectively suppressed. A more preferable range is a range of 0.1 ppm or more and 25 ppm or less, further preferably 1 ppm to 20 ppm, particularly preferably 5 ppm to 15 ppm.

The content n of the quaternary ammonium compound (A) in terms of nitrogen is represented by the following expression (I):

$$n = S \times 14/T \qquad (I)$$

wherein S represents the amount (ppm or ppb by mass) of the quaternary ammonium compound (A) based on the total amount of polyacetal and the quaternary ammonium compound (A), 14 represents the atomic weight of nitrogen, and T represents the molecular weight of the quaternary ammonium compound.

The content of the quaternary ammonium compound (A) is here defined by the amount in terms of nitrogen in order to avoid the number of moles of the quaternary compound included in the resin composition from being considerably varied depending on the molecular weight of the quaternary ammonium compound (A).

Herein, the amount of nitrogen derived from the quaternary ammonium compound (A) in the polyacetal resin composition can be quantitatively determined by, for example, NMR analysis as follows.

After 15 kg of a polyacetal resin composition pellet is frozen and pulverized by a Linrex mill or the like, the pellet is loaded in a 100-L autoclave made of SUS, equipped with a stirrer, and 50 L of distilled water is loaded therein. Thereafter, the resultant is loaded in an oven set at 120° C., left to stand for 24 hours, thereafter cooled to room temperature, and subjected to solid-liquid separation by suction filtration. The resulting liquid is concentrated by an evaporator to about 5 ml, a liquid where about 2.5 ml of the concentrated liquid and heavy water are mixed at 1:1 (volume ratio) is subjected to NMR analysis, and the amount of nitrogen derived from the quaternary ammonium compound (A) is quantitatively determined from peak areas around 3.5 ppm and around 3.9 ppm.

When it is clear that the nitrogen source is only the quaternary ammonium compound (A), the amount of nitrogen can also be quantitatively determined by quantitatively determining the atomic weight of nitrogen by a nitrogen analyzer (for example, a nitrogen analyzer TN-2100H manufactured by Mitsubishi Chemical Analytech Co., Ltd.).

When the polyacetal resin composition of the present embodiment includes a quaternary ammonium compound (C) represented by formula (3), the concentration of the quaternary ammonium compound (C) in the polyacetal resin composition is preferably 0.5 ppb by mass to 500 ppm by mass in terms of the concentration n''' of nitrogen derived from the quaternary ammonium compound (C), represented by the following expression (II):

$$n'''=S'''\times 14/T''' \quad (II)$$

wherein S''' represents the amount (ppb or ppm by mass) of the quaternary ammonium compound (C) based on the total amount of polyacetal and the quaternary ammonium compound (C), 14 represents the atomic weight of nitrogen, and T''' represents the molecular weight of the quaternary ammonium compound (C).

When the concentration n''' of the quaternary ammonium compound (C) is 0.5 ppb by mass or more, the effect of enhancing the decomposition rate of an unstable terminal portion of polyacetal by combination use with the quaternary ammonium compound (C) is exerted. When the concentration is 500 ppm by mass or less, the color tone of polyacetal is not impaired even after stabilization.

The concentration of the quaternary ammonium compound (C) is here defined by the amount in terms of nitrogen in order to avoid the number of moles of the quaternary ammonium compound (C) relative to polyacetal from being varied depending on the molecular weight of the quaternary ammonium compound (C).

As described above, even polyacetal having an unstable terminal group can allow generation of formaldehyde and the like due to a heating treatment to be reduced in use in the form of a resin composition in which the quaternary ammonium compound (agent for suppression of generation of a volatile organic compound from polyacetal) of the present embodiment coexists.

The quaternary ammonium composition of the present embodiment can include, if necessary, a heat stabilizer, an antioxidant, a formaldehyde scavenger, a formic acid scavenger, an ultraviolet absorber, a light stabilizer, a release agent, a reinforcing material, a conducting material, a thermoplastic resin, a thermoplastic elastomer, and a pigment.

Examples of the heat stabilizer include an antioxidant, a formaldehyde or formic acid scavenger, or combination use thereof, and combination use of an antioxidant and a scavenger is preferable.

The antioxidant is preferably a hindered phenol-based antioxidant, and examples thereof include n-octadecyl-3-(3',5'-di-t-butyl-4'-hydroxyphenyl)-propionate, n-octadecyl-3-(3'-methyl-5-t-butyl-4'-hydroxyphenyl)-propionate, n-tetradecyl-3-(3',5'-di-t-butyl-4'-hydroxyphenyl)-propionate, 1,6-hexanediol-bis-(3-(3,5-di-t-butyl-4-hydroxyphenyl)-propionate), 1,4-butanediol-bis-(3-(3,5-di-t-butyl-4-hydroxyphenyl)-propionate), triethylene glycol-bis-(3-(3-t-butyl-5-methyl-4-hydroxyphenyl)-propionate), tetrakis-(methylene-3-(3',5'-di-t-butyl-4'-hydroxyphenyl)propionate methane, 3,9-bis(2-(3-(3-t-butyl-4-hydroxy-5-methylphenyl)propionyloxy)-1,1-dimethylethyl)2,4,8,10-tetraoxaspiro (5,5)undecane, N,N'-bis-3-(3',5'-di-t-butyl-4-hydroxyphenol)propionyl hexamethylenediamine, N,N'-tetramethylenebis-3-(3'-methyl-5'-t-butyl-4-hydroxyphenol) propionyldiamine, N,N'-bis-(3-(3,5-di-t-butyl-4-hydroxyphenol)propionyl)hydrazine, N-salicyloyl-N'-salicylidene hydrazine, 3-(N-salicyloyl)amino-1,2,4-triazole, and N,N'-bis(2-(3-(3,5-di-butyl-4-hydroxyphenyl) propionyloxy)ethyl)oxyamide.

Among these hindered phenol-based antioxidants, triethylene glycol-bis-(3-(3-t-butyl-5-methyl-4-hydroxyphenyl)-propionate) and tetrakis-(methylene-3-(3',5'-di-t-butyl-4'-hydroxyphenyl)propionate methane are preferable.

Specific examples of the formaldehyde or formic acid scavenger include (i) formaldehyde reactive nitrogen-containing compound and polymer, and (ii) hydroxide, an inorganic acid salt, a carboxylic acid salt, and alkoxide of an alkali metal or alkaline-earth metal.

Examples of the formaldehyde reactive nitrogen-containing compound (i) include (1) dicyandiamide, (2) amino-substituted triazine, and (3) a co-condensate of amino-substituted triazine and formaldehyde.

Specific examples of the amino-substituted triazine (2) include guanamine (2,4-diamino-sym-triazine), melamine (2,4,6-triamino-sym-triazine), N-butylmelamine, N-phenylmelamine, N,N-diphenylmelamine, N,N-diallylmelamine, N,N',N''-triphenylmelamine, N-methylolmelamine, N,N'-dimethylolmelamine, N,N',N''-trimethylolmelamine, benzoguanamine (2,4-diamino-6-phenyl-sym-triazine), 2,4-diamino-6-methyl-sym-triazine, 2,4-diamino-6-butyl-sym-triazine, 2,4-diamino-6-benzyloxy-sym-triazine, 2,4-diamino-6-butoxy-sym-triazine, 2,4-diamino-6-cyclohexyl-sym-triazine, 2,4-diamino-6-chloro-sym-triazine, 2,4-diamino-6-mercapto-sym-triazine, 2,4-dioxy-6-amino-sym-triazine (ammelite), 2-oxy-4,6-diamino-sym-triazine (ameline), and N,N',N'-tetracyanoethylbenzoguanamine. Specific examples of the co-condensate (3) of amino-substituted triazine and formaldehyde include a melamine-formaldehyde polycondensate. In particular, dicyandiamide, melamine, and a melamine-formaldehyde polycondensate are preferable.

Examples of the formaldehyde reactive nitrogen group-containing polymer (i) include (1) a polyamide resin, (2) a polymer obtained by polymerizing acrylamide and a derivative thereof, or acrylamide and a derivative thereof and other vinyl monomer, in the presence of metal alcholate, (3) a polymer obtained by polymerizing acrylamide and a derivative thereof, or acrylamide and a derivative thereof and other vinyl monomer, in the presence of radical polymerization, and (4) a polymer containing a nitrogen group such as amine, amide, urea, and urethane.

Specific examples of the polyamide resin (1) include nylon 4-6, nylon 6, nylon 6-6, nylon 6-10, nylon 6-12, nylon 12, and copolymerized products thereof, as well as nylon 6/6-6, nylon 6/6-6/6-10, and nylon 6/6-12. Specific examples of the polymer (2) obtained by polymerizing acrylamide and a derivative thereof, or acrylamide and a derivative thereof and other vinyl monomer, in the presence of metal alcholate, include a poly-β-alanine copolymer. Such a polymer can be produced by any method described in Japanese Patent Publication No. 6-12259, Japanese Patent Publication No. 5-87096, Japanese Patent Publication No. 5-47568, and Japanese Patent Laid-Open No. 3-234729. The polymer (3) obtained by polymerizing acrylamide and a derivative thereof, or acrylamide and a derivative thereof and other vinyl monomer, in the presence of radical polymerization, can be produced by any method described in Japanese Patent Laid-Open No. 3-28260.

Specific examples of the hydroxide, inorganic acid salt, carboxylic acid salt, and alkoxide of an alkali metal or an alkaline-earth metal (ii) include hydroxide of sodium, potassium, magnesium, calcium, or barium, and carbonic acid salts, phosphoric acid salts, silicic acid salts, boric acid salts, and carboxylic acid salts of such metals. The carboxylic acid in the carboxylic acid salt is, for example, a saturated or unsaturated aliphatic carboxylic acid having 10 to 36 carbon atoms, and such a carboxylic acid may be substituted with a hydroxyl group. Examples of the saturated aliphatic carboxylic acid include capric acid, lauric acid, myristic acid, palmitic acid, stearic acid, arachidic acid, behenic acid, lignoceric acid, cerotic acid, montanic acid, melissic acid, and ceroplastic acid. Examples of the unsaturated aliphatic carboxylic acid include undecylenic acid, oleic acid, elaidic acid, cetoleic acid, erucic acid, brassidic acid, sorbic acid, linoleic acid, linolenic acid, arachadonic acid, propiolic acid, and stearolic acid. Examples of the alkoxide include methoxides and ethoxides of the above metals.

Examples of a weather-resistant (light) stabilizer include (i) a benzotriazole-based substance, (ii) an oxalic acid anilide-based substance, and (iii) a hindered amine-based substance.

Specific examples of the benzotriazole-based substance (i) include 2-(2'-hydroxy-5'-methyl-phenyl)benzotriazole, 2-[2'-hydroxy-3,5-di-t-butyl-phenyl)benzotriazole, 2-[2'-hydroxy-3,5-di-isoamyl-phenyl)benzotriazole, 2-[2'-hydroxy-3,5-bis-(α,α-dimethylbenzyl)phenyl]-2H-benzotriazole, and 2-(2'-hydroxy-4'-octoxyphenyl)benzotriazole, and preferably include 2-[2'-hydroxy-3,5-bis-(α,α-dimethylbenzyl)phenyl]-2H-benzotriazole and 2-[2'-hydroxy-3,5-di-t-butyl-phenyl)benzotriazole.

Specific examples of the oxalic acid anilide-based substance (ii) include 2-ethoxy-2'-ethyloxalic acid bisanilide, 2-ethoxy-5-t-butyl-2'-ethyloxalic acid bisanilide, and 2-ethoxy-3'-dodecyloxalic acid bisanilide. Such substances may be each used singly or in combinations of two or more kinds thereof.

Specific examples of the hindered amine-based substance (iii) include 4-acetoxy-2,2,6,6-tetramethylpiperidine, 4-stearoyloxy-2,2,6,6-tetramethylpiperidine, 4-acryloyloxy-2,2,6,6-tetramethylpiperidine, 4-(phenylacetoxy)-2,2,6,6-tetramethylpiperidine, 4-benzoyloxy-2,2,6,6-tetramethylpiperidine, 4-methoxy-2,2,6,6-tetramethylpiperidine, 4-stearyloxy-2,2,6,6-tetramethylpiperidine, 4-cyclohexyloxy-2,2,6,6-tetramethylpiperidine, 4-benzyloxy-2,2,6,6-tetramethylpiperidine, 4-phenoxy-2,2,6,6-tetramethylpiperidine, 4-(ethylcarbamoyloxy)-2,2,6,6-tetramethylpiperidine, 4-(cyclohexylcarbamoyloxy)-2,2,6,6-tetramethylpiperidine, 4-(phenylcarbamoyloxy)-2,2,6,6-tetramethylpiperidine, bis(2,2,6,6-tetramethyl-4-piperidine)-carbonate, bis(2,2,6,6-tetramethyl-4-piperidyl)-oxalate, bis(2,2,6,6-tetramethyl-4-piperidyl)-malonate, bis(2,2,6,6-tetramethyl-4-piperidyl)-sebacate, bis(2,2,6,6-tetramethyl-4-piperidyl)-adipate bis(2,2,6,6-tetramethyl-4-piperidyl)-terephthalate, 1,2-bis(2,2,6,6-tetramethyl-4-piperidyloxy)-ethane, α,α'-bis(2,2,6,6-tetramethyl-4-piperidyloxy)-p-xylene, bis(2,2,6,6-tetramethyl-4-piperidyl)tolylene-2,4-dicarbamate, bis(2,2,6,6-tetramethyl-4-piperidyl)-hexamethylene-1,6-dicarbamate, tris(2,2,6,6-tetramethyl-4-piperidyl)-benzene-1,3,5-tricarboxylate, and tris(2,2,6,6-tetramethyl-4-piperidyl)-benzene-1,3,4-tricarboxylate, and bis(2,2,6,6-tetramethyl-4-piperidyl)-sebacate is preferable. Such hindered amine-based substances may be each used singly or in combinations of two or more kinds thereof.

A combination of the benzotriazole-based substance or the oxalic acid anilide-based substance with the hindered amine-based substance is more preferable.

Examples of the release agent include an alcohol, an ester of an alcohol and a fatty acid, an ester of an alcohol and a dicarboxylic acid, and silicone oil.

Specific examples of the alcohol include a monohydric alcohol and a polyhydric alcohol, and examples of the monohydric alcohol include octyl alcohol, capryl alcohol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, oleyl alcohol, nonadecyl alcohol, eicosyl alcohol, behenyl alcohol, ceryl alcohol, melissyl alcohol, 2-hexyldecanol, 2-octyldodecanol, 2-decyltetradecanol, and unilin alcohol. The polyhydric alcohol is a polyhydric alcohol containing 2 to 6 carbon atoms, and examples include ethylene glycol, diethylene glycol, triethylene glycol, propylene glycol, dipropylene glycol, butanediol, pentanediol, hexanediol, glycerin, diglycerin, triglycerin, threitol, erythritol, pentaerythritol, arabitol, ribitol, xylitol, sorbit, sorbitan, sorbitol, and mannitol.

As the ester of an alcohol and a fatty acid, preferable is a fatty acid ester derived from a fatty acid selected from palmitic acid, stearic acid, behenic acid, and montanic acid, among fatty acid compounds, and a polyhydric alcohol selected from glycerin, pentaerythritol, sorbitan, and sorbitol. Such a fatty acid ester compound may have a hydroxyl group or no hydroxyl group, and the fatty acid ester compound is not limited. For example, a monoester, a diester, or a trimester may be adopted. A hydroxyl group may be blocked by boric acid or the like.

Specific examples of preferable fatty acid esters include glycerin monopalmitate, glycerin dipalmitate, glycerin tripalmitate, glycerin monostearate, glycerin distearate, glycerin tristearate, glycerin monobehenate, glycerin dibehenate, glycerin tribehenate, glycerin monomontanate, glycerin dimontanate, glycerin trimontanate, pentaerythritol monopalmitate, pentaerythritol dipalmitate, pentaerythritol tripalmitate, pentaerythritol tetrapalmitate, pentaerythritol monostearate, pentaerythritol distearate, pentaerythritol tristearate, pentaerythritol tetrastearate, pentaerythritol monobehenate, pentaerythritol dibehenate, pentaerythritol tribehenate, pentaerythritol tetrabehenate, pentaerythritol monomontanate, pentaerythritol dimontanate, pentaerythritol trimontanate, pentaerythritol tetramontanate, sorbitan monopalmitate, sorbitan dipalmitate, sorbitan tripalmitate, sorbitan monostearate, sorbitan distearate, sorbitan tristearate, sorbitan monobehenate, sorbitan dibehenate, sorbitan tribehenate, sorbitan monomontanate, sorbitan dimontanate, sorbitan trimontanate, sorbitol monopalmitate, sorbitol dipalmitate, sorbitol tripalmitate, sorbitol monostearate, sorbitol distearate, sorbitol tristearate, sorbitol monobehenate, sorbitol dibehenate, sorbitol tribehenate sorbitol monomontanate, sorbitol dimontanate, and sorbitol trimontanate.

Examples of the aliphatic ester compound where a hydroxyl group is blocked by boric acid or the like also include a boric acid ester of glycerin monofatty acid ester. Examples of the ester of an alcohol and a dicarboxylic acid include monoesters and diesters of saturated/unsaturated alcohols as alcohols, such as methyl alcohol, ethyl alcohol, propyl alcohol, n-butyl alcohol, isobutyl alcohol, t-butyl alcohol, n-amyl alcohol, 2-pentanol, n-heptyl alcohol, n-octyl alcohol, n-nonyl alcohol, lauryl alcohol, myristyl alcohol, cetyl alcohol, stearyl alcohol, and behenyl alcohol, and oxalic acid, malonic acid, succinic acid, glutaric acid, adipic acid, pimelic acid, suberic acid, azelaic acid, sebacid acid, undecanoic acid, brassylic acid, maleic acid, fumaric acid, and glutaconic acid, as dicarboxylic acids.

5. Method for Producing Polyacetal

The polyacetal can be produced using not in the form of the resin composition, but in the form of a polyacetal stabilized in advance (as a stabilized polyacetal) by use of a polyacetal having a thermally unstable terminal portion with the quaternary ammonium compound (A) or the quaternary ammonium composition of the present embodiment.

Specifically, a polyacetal having a thermally unstable terminal portion can be stabilized by a heat treatment in the presence of the quaternary ammonium compound (A)/quaternary ammonium composition of the present embodiment.

Hereinafter, a method for producing polyacetal of the present embodiment, including a step of subjecting a polyacetal having a thermally unstable terminal portion (hereinafter, sometimes referred to as "crude polyacetal".) in the present embodiment to a heat treatment in the presence of the quaternary ammonium compound (A) or the quaternary ammonium composition will be described with reference to specific examples.

In the present embodiment, a step of obtaining a crude polyacetal by (co)polymerization can be included. The (co)polymerization method here is not limited, and the crude polyacetal can be obtained by polymerization according to an ordinary method. Hereinafter, a material which can be preferably used in production of a crude polyacetal (step of obtaining polyacetal by (co)polymerization) will be described.

<Trioxane>

Trioxane is a cyclic trimer of formaldehyde, and is generally obtained by reacting an aqueous formalin solution in the presence of an acidic catalyst.

The trioxane may sometimes contain impurities having a chain transfer action, such as water, methanol, formic acid, and methyl formate, and therefore these impurities are preferably removed for purification by a method such as distillation at a stage before a step of performing a polymerization reaction.

In this case, the total amount of the impurities having a chain transfer action is preferably $1\times10^{-3}$ mol or less, more preferably $0.5\times10^{-3}$ mol or less based on 1 mol of the trioxane.

Reducing the amount of the impurities as to the above value can result in a sufficient enhancement in polymerization reaction rate for practical use, thereby providing a polyacetal having excellent heat stability.

<Cyclic Ether and/or Cyclic Formal>

When the polyacetal is a copolymer, a cyclic ether and/or a cyclic formal can be used as the comonomer. These are each a component copolymerizable with formaldehyde and the trioxane.

Examples of the cyclic ether or cyclic formal include, but are not limited to the following, ethylene oxide, propylene oxide, butylene oxide, epichlorohydrin, epibromohydrin, styrene oxide, oxetane, 1,3-dioxolane, ethylene glycol formal, propylene glycol formal, diethylene glycol formal, triethylene glycol formal, 1,4-butanediol formal, 1,5-pentanediol formal, and 1,6-hexanediol formal. From the viewpoint of availability, 1,3-dioxolane and 1,4-butanediol formal are preferable. These may be used singly or in combinations of two or more kinds thereof.

The amount of the cyclic ether and/or cyclic formal added is preferably in the range from $1\times10^{-2}$ to $20\times10^{-2}$ mol, more preferably $1\times10^{-2}$ to $15\times10^{-2}$ mol, further preferably $1\times10^{-2}$ to $10\times10^{-2}$ mol, still more preferably $1\times10^{-2}$ to $5\times10^{-2}$ mol based on 1 mol of the trioxane from the viewpoint of the mechanical strength of the resulting polyacetal copolymer.

<Polymerization Catalyst>

Examples of the polymerization catalyst for use in the step of obtaining polyacetal by (co)polymerization include boric acid, tin, titanium, phosphorus, arsenicum, and antimonide, represented by Lewis acid. In particular, boron trifluoride, boron trifluoride-based hydrate, and a coordinated complex compound of an organic compound including an oxygen atom or a sulfur atom, with boron trifluoride are preferable from the viewpoint of availability, and specific preferable examples include boron trifluoride, boron trifluoride diethyl etherate, and boron trifluoride-di-n-butyl etherate. These may be used singly or in combinations of two or more kinds thereof.

The amount of the polymerization catalyst added is preferably in the range from $0.1\times10^{-5}$ to $0.1\times10^{-3}$ mol, more preferably in the range from $0.3\times10^{-5}$ to $0.5\times10^{-4}$ mol, further preferably in the range from $0.5\times10^{-5}$ to $0.4\times10^{-4}$ mol based on 1 mol of the trioxane.

The amount of the polymerization catalyst added can be in the above range, thereby allowing a polymerization reaction to be stably performed for a long time with the amount of scale generated in a feeding section of a polymerization reactor being reduced.

<Low-Molecular Weight Acetal>

In the step of obtaining polyacetal by (co)polymerization, a low-molecular weight acetal represented by the following general formula can also be used:

R—(CH$_2$—O)$n$-R wherein R represents any one selected from the group consisting of hydrogen, a branched or straight alkyl group, a branched or straight alkoxy group, and a hydroxyl group; and n represents an integer of 1 or more and 20 or less.

The low-molecular weight acetal serves as a chain transfer agent in a polymerization step, and is an acetal having a molecular weight of 200 or less, preferably 60 to 170. Such an acetal having the molecular weight can be used to thereby adjust the molecular weight of polyacetal to be finally intended.

Examples of the low-molecular weight acetal represented by the general formula include, but are not limited to the following, methylal, methoxymethylal, dimethoxymethylal, and trimethoxymethylal. These may be used singly or in combinations of two or more kinds thereof.

The amount of the low-molecular weight acetal represented by the general formula, added, is preferably in the range from $0.1 \times 10^{-4}$ to $0.6 \times 10^{-2}$ mol, more preferably in the range from $0.1 \times 10^{-4}$ to $0.6 \times 10^{-3}$ mol, further preferably in the range from $0.1 \times 10^{-4}$ to $0.1 \times 10^{-3}$ mol based on 1 mol of the trioxane from the viewpoint that the molecular weight of the polyacetal to be intended is controlled within a suitable range.

In the present embodiment, a crude polyacetal is subjected to a heat treatment in the presence of the quaternary ammonium compound (A) or the quaternary ammonium composition, and is thus stabilized.

The mode of the heat treatment is not limited, but examples thereof can include the following two modes.

One mode thereof includes heating and melting a crude polyacetal in the presence of the quaternary ammonium compound (A)/quaternary ammonium composition, and another mode thereof includes heating a crude polyacetal in the form of slurry in the presence of the quaternary ammonium compound (A)/quaternary ammonium composition.

First, a heat treatment to be performed with a crude polyacetal being in a molten state is described.

The crude polyacetal can be molten by, for example, a single-screw type extruder equipped with a vent, or a twin-screw type extruder equipped with a vent. The heat treatment is preferably performed at a temperature which is higher than the melting point of polyacetal and which is 260° C. or less. If the temperature exceeds 260° C., the problem of coloration, and the problem of decomposition of the main chain of a polymer (a decrease in molecular weight) may be caused. In this case, the quaternary ammonium compound (A)/quaternary ammonium composition may be added to the crude polyacetal in advance before melting of the crude polyacetal, or the quaternary ammonium compound (A)/quaternary ammonium composition may be added to the crude polyacetal molten after the crude polyacetal is molten.

Examples of the method where the quaternary ammonium compound (A)/quaternary ammonium composition is added in advance to the crude polyacetal before melting can include a method where a solution obtained by dissolving the quaternary ammonium compound (A)/quaternary ammonium composition in water or an organic solvent which can dissolve the quaternary ammonium compound (A)/quaternary ammonium composition, specifically, a lower aliphatic alcohol or the like (for example, methanol) is added in an amount of 0.1 to 5% by mass relative to the crude polyacetal, and thereafter the resultant is mixed. In such a case, the mixing may be performed using a common solid mixer such as a horizontal cylinder type, V-shaped, ribbon type, paddle type, or high speed flow type mixer. Alternatively, a solution containing the quaternary ammonium compound (A)/quaternary ammonium composition may be directly added to a shooting unit through which polyacetal is fed to an extruder, or may be directly added to the main body of an extruder through a feeding port of an extruder until polyacetal is molten.

Examples of other method where the quaternary ammonium compound (A)/quaternary ammonium composition is added in advance to the crude polyacetal before melting can include a method where the crude polyacetal is loaded into a solution of the quaternary ammonium compound (A)/quaternary ammonium composition in water or the organic solvent (lower aliphatic alcohol such as methanol) to form a slurry once, and the slurry is filtered and dried to thereby allow the quaternary ammonium compound (A)/quaternary ammonium composition to remain in the polyacetal before melting. The solvent here used in the solution is preferably a solvent which cannot dissolve the crude polyacetal. Such a solvent can be used to thereby allow a post-treatment such as filtration and drying to be easily performed.

The amount of the quaternary ammonium compound (A) used based on the total mass of the crude polyacetal and the quaternary ammonium compound (A)/quaternary ammonium composition can be controlled to a specified amount used, by controlling the concentration of the quaternary ammonium compound (A) in the solution and the liquid content in the polyacetal after filtration.

According to the above method, a crude polyacetal to which a predetermined amount of the quaternary ammonium compound (A) is added is molten by an extruder or the like as it is, or, if necessary, after drying, and is subjected to a heat treatment. During the melting, at least one of amines, water, methanol, and the like, each being a conventionally known decomposition accelerator, may be added for stabilization, or the crude polyacetal may be subjected to a heat treatment without any substances added. The amount of a decomposition accelerator conventionally used, such as amines, water, or methanol, added is preferably 0.1 to 5 parts by mass based on 100 parts by mass of the polyacetal. Another quaternary ammonium compound (quaternary ammonium compound (C) or the like) may be, if necessary, further added. Such decomposition accelerators, for example, amines, water, methanol, and the quaternary ammonium compound may be each added singly or in combinations of two or more kinds thereof.

On the other hand, examples of the method where the quaternary ammonium compound (A)/quaternary ammonium composition is added to the crude polyacetal in a molten state after the crude polyacetal is molten can include a method where a solution obtained by dissolving the quaternary ammonium compound (A)/quaternary ammonium composition in water or an organic solvent which can dissolve the quaternary ammonium compound (A)/quaternary ammonium composition, specifically, a lower aliphatic alcohol or the like (for example, methanol) is added, and a method where the quaternary ammonium composition compound (A)/quaternary ammonium, and water or an organic solvent which can dissolve the quaternary ammonium compound (A)/quaternary ammonium composition are each separately added to the polyacetal molten by an extruder or the like.

The amount of water or an organic solvent such as methanol, added, is preferably about 0.1 to 5 parts by mass based on 100 parts by mass of the crude polyacetal. Not only the quaternary ammonium compound (A)/quaternary ammonium composition, but also conventionally known amines, and another quaternary ammonium compound (quaternary ammonium compound (C) or the like) may be added.

In the present embodiment, the amount of the quaternary ammonium compound (A) used in the heat treatment step is not limited, and the concentration of the quaternary ammonium compound (A) is preferably 0.1 ppb by mass to 30 ppm by mass, more preferably 0.1 ppm by mass to 25 ppm by mass, further preferably 1 ppm by mass to 20 ppm by mass, particularly preferably 5 ppm to 10 ppm in terms of the concentration n' of nitrogen derived from the quaternary ammonium compound (A), represented by the following expression (I'):

$$n' = S' \times 14/T' \qquad (I')$$

wherein S' represents the amount (ppb or ppm by mass) of the quaternary ammonium compound (A) based on the total mass of the crude polyacetal and the quaternary ammonium compound (A), 14 represents the atomic weight of nitrogen, and T' represents the molecular weight of the quaternary ammonium compound (A).

When the concentration n' of nitrogen derived from the quaternary ammonium compound (A) is 0.1 ppb by mass or more, an unstable terminal portion can be decomposed in a short time, and when the concentration is 30 ppm by mass or less, the color tone of polyacetal is not impaired even after stabilization.

The concentration of the quaternary ammonium compound (A) is here expressed in terms of the concentration of nitrogen in order to avoid the dependence on the molecular weight of the quaternary ammonium compound (A) as in the above.

Next, a heat treatment to be performed with a crude polyacetal being not molten, but in a slurry state, is described.

Examples of such a heat treatment can include a process where polyacetal is loaded into a solution obtained by dissolving the quaternary ammonium compound (A)/quaternary ammonium composition in a medium which cannot dissolve polyacetal, and the polyacetal not molten, but in a slurry state, is subjected to a heating treatment.

A solvent which cannot dissolve the crude polyacetal is here used as the solvent for use in the solution in order to enable a post-treatment such as filtration and drying to be easily performed by use of such a solvent, as in the above. Examples of the medium which cannot dissolve polyacetal include water, and an aqueous solution containing about 10 to 30% by mass of methanol.

The heating temperature is not limited, and the heat treatment is preferably performed at a temperature which is 80° C. or more and less than the melting point of polyacetal.

The concentration of polyacetal in the slurry (slurry concentration) is usually selected to be 5 to 50% by mass. If the slurry concentration is less than 5% by mass, a large amount of the medium which cannot dissolve polyacetal is needed to result in an increase in the size of an apparatus. If the slurry concentration exceeds 50% by mass, the following problem is caused: stirring and mixing are insufficiently made to thereby precipitate polyacetal, resulting in two-phase separation of the slurry.

The amount of the quaternary ammonium compound (A)/quaternary ammonium composition in the slurry is not limited, and the concentration of the quaternary ammonium compound (A) is preferably 0.5 ppb by mass to 500 ppm by mass, more preferably 1 ppm by mass to 300 ppm by mass in terms of the concentration n" of nitrogen derived from the quaternary ammonium compound (A), represented by the following expression (I"):

$$n'' = S'' \times 14/T'' \qquad (I'')$$

wherein S" represents the concentration (ppb or ppm by mass) of the quaternary ammonium compound (A) in the solution, 14 represents the atomic weight of nitrogen, and T" represents the molecular weight of the quaternary ammonium compound.

When the concentration n" of nitrogen derived from the quaternary ammonium compound (A) is 0.5 ppb by mass or more, an unstable terminal portion can be decomposed in a short time, and when the concentration is 500 ppm by mass or less, the color tone of polyacetal is not impaired even after stabilization.

The concentration of the quaternary ammonium compound (A) is here expressed in terms of the concentration of nitrogen in order to avoid the dependence on the molecular weight of the quaternary ammonium compound (A) as in the above.

Amines conventionally used, a quaternary ammonium compound (C) described below, and the like may be used in combination for the solution obtained by dissolving the quaternary ammonium composition in the medium which cannot dissolve polyacetal.

In stabilization of the crude polyacetal not molten, but in a slurry state, a polyacetal after the heat treatment is subjected to a post-treatment, such as filtration and washing, for removal of formaldehyde and/or an unreacted monomer generated from the terminal portion by decomposition, and thereafter is dried. In stabilization in a molten state, a polyacetal after the heat treatment is subjected to removal of the above formaldehyde and unreacted monomer, an excess of the quaternary ammonium compound (A)/quaternary ammonium composition, and the like under reduced pressure by a vent, and thereafter is pelletized.

In the method for producing polyacetal of the present embodiment, the heat treatment step in the presence of the quaternary ammonium compound (A)/quaternary ammonium composition may be performed after the polymerization catalyst remaining in a crude polyacetal obtained by a polymerization reaction is deactivated, or with the polymerization catalyst being not deactivated.

Furthermore, the method for producing polyacetal of the present embodiment may include a known stabilization treatment, and in this case, the heat treatment step in the presence of the quaternary ammonium compound (A)/quaternary ammonium composition may also be applied to a polyacetal in which an unstable terminal portion still partially remains even after the known stabilization treatment.

Deactivation of the polymerization catalyst can be performed by loading the crude polyacetal obtained by a polymerization reaction into an aqueous solution or organic solvent solution containing at least one of amines such as ammonia, triethylamine or tri-n-butylamine, or a catalyst neutralizer/deactivator such as a hydroxide, an inorganic acid salt, or an organic acid salt of an alkali metal or alkaline-earth metal, and stirring the resultant in a slurry state generally for several minutes to several hours. In this case, the slurry after catalyst neutralization/deactivation is subjected to removal of the unreacted monomer, the catalyst neutralizer/deactivator, and a salt due to neutralization of the catalyst, by filtration and/or washing, and thereafter is dried.

A method where vapor of ammonia, triethylamine, and the like is brought into contact with the crude polyacetal, to deactivate the polymerization catalyst, or a method where at least one of hindered amines, triphenyl phosphine, and calcium hydroxide is brought into contact with the crude polyacetal in a mixer, to deactivate the catalyst can also be used. The above stabilization method may also be performed using a polyacetal in which the polymerization catalyst is volatilized and decreased by heating at a temperature equal to or lower than the melting point of the crude polyacetal under an inert gas atmosphere without deactivation of the polymerization catalyst.

The deactivation operation of the polymerization catalyst and the volatilization and decreasing operation of the polymerization catalyst may be performed, if necessary, after the crude polyacetal obtained by a polymerization reaction is pulverized.

The heat treatment step (stabilization of polyacetal) can be performed by appropriately using conventionally known apparatus and operation method. Conventionally known amines such as ammonia and triethylamine may be further used in combination.

The quaternary ammonium compound (A) and the quaternary ammonium composition are particularly preferably used with being dissolved in water in the heat treatment step (stabilization of polyacetal).

Use of an aqueous solution of the quaternary ammonium compound (A)/quaternary ammonium composition in stabilization of crude polyacetal enables removal of formaldehyde generated from polyacetal to be promoted because formaldehyde is in an azeotropic state with water.

In addition, use of an aqueous solution of the quaternary ammonium (A)/quaternary ammonium composition enables a step of removing water by absolute drying in production not to be needed, thereby saving heat energy and preventing deterioration/discoloration of the quaternary ammonium compound (A)/quaternary ammonium composition.

When a quaternary ammonium compound (C) represented by formula (3) is used in combination in the heat treatment step (stabilization of polyacetal), the amount of the quaternary ammonium compound (C) used is preferably 0.5 ppb by mass to 500 ppm by mass in terms of the concentration n'''' of nitrogen derived from the quaternary ammonium compound (C), represented by the following expression (II'):

$$n''''=S''''\times 14/T'''' \qquad (II')$$

wherein S'''' represents the amount (ppb or ppm by mass) of the quaternary ammonium compound (C) based on the total mass of the crude polyacetal and the quaternary ammonium compound (C), 14 represents the atomic weight of nitrogen, and T'''' represents the molecular weight of the quaternary ammonium compound (C).

When the amount n'''' of the quaternary ammonium compound (C) used is 0.5 ppb by mass or more, the effect of enhancing the decomposition rate of an unstable terminal portion of polyacetal by combination use with the quaternary ammonium compound (C) is exerted. When the amount is 500 ppm by mass or less, the color tone of polyacetal is not impaired even after stabilization.

The amount of the quaternary ammonium compound (C) used is here defined by the amount in terms of nitrogen in order to avoid the number of moles of the quaternary ammonium compound (C) relative to polyacetal from being varied depending on the molecular weight of the quaternary ammonium compound (C).

The stable polyacetal obtained as described above is generally, if necessary, mixed with one or more compounding agents such as an antioxidant, a formaldehyde scavenger, a formic acid scavenger, an ultraviolet absorber, a heat stabilizer, a light stabilizer, a release agent, a reinforcing material, a conducting material, a thermoplastic resin, a thermoplastic elastomer, and a pigment by an extruder or the like, and is then put into practical use.

The point of time at which the compounding agents are compounded is not particularly limited, and, for example, the compounding agents may be added in advance to a crude polyacetal before an unstable terminal portion is decomposed and removed, or may be added to a polyacetal from which an unstable terminal portion is decomposed and removed, depending on the types thereof.

Next, a terminal group contained in a polyacetal which can be stabilized by the quaternary ammonium compound (A) of the present embodiment is described.

Examples of the terminal group contained in the entire of a plurality of polyacetal (co)polymer chains forming the polyacetal include not only the above group including a hydroxymethyl group, such as a —$CH_2OH$ group or a —$(OCH_2)_n$—OH group, but also an alkoxyl group such as a methoxyl group (—$OCH_3$), a hydroxyalkyl group such as a hydroxyethyl group (—$CH_2CH_2OH$), and a formate group.

A terminal alkoxyl group is generally formed from formal being a molecular weight modifier to be added at a polymerization stage. For example, when methylal (($CH_3O)_2CH_2$) is used as a molecular weight modifier, a methoxyl group is formed as the terminal group. The terminal alkoxyl group generally has 1 to 10, particularly 1 to 3 carbon atoms in terms of synthesis and purification of formal being a molecular weight modifier.

A terminal hydroxyalkyl group such as a hydroxyethyl group or a hydroxybutyl group is derived from the cyclic ether or cyclic formal for use in a raw material comonomer of polyacetal, and is formed in the following process.

That is, when a polyacetal where an oxyalkylene group derived from the cyclic ether or cyclic formal is inserted in a repeated polyacetal unit is obtained by polymerization, a thermally unstable terminal hydroxymethyl group (—$CH_2OH$) is first generated due to a trace amount of water or the like in the raw material. The unstable portion at a terminal is decomposed by a stabilization treatment, and such decomposition progresses inward to a main chain including a polyacetal unit and an oxyalkylene unit, and reaches a site of the oxyalkylene unit, thereby allowing the oxyalkylene unit at the site to be converted to a stable terminal hydroxyalkyl group such as a hydroxyethyl group or a hydroxybutyl group. The hydroxyalkyl group has at least 2, generally 2 to 10 carbon atom in terms of synthesis and purification of the cyclic ether and cyclic formal.

On the other hand, a hydroxymethyl group, if present as a terminal group in polyacetal, is eliminated from the terminal when heated particularly by molding or the like, to generate formaldehyde. Therefore, a terminal hydroxymethyl group, if present in a large amount, excessively generates formaldehyde.

The quaternary ammonium compound (A) having R2, of the present embodiment, serves to suppress such generation, and the terminal hydroxymethyl group is considered to be decomposed and removed due to the action of the quaternary ammonium compound (A), thereby resulting in suppression of generation of formaldehyde.

Furthermore, it is considered that the quaternary ammonium compound (A) of the present embodiment involves in not only the decomposition and removal of the terminal hydroxymethyl group, but also formation of trace amounts of formaldehyde, acetaldehyde, and acrolein generated from a trace amount of an unstable terminal which is not removed and remains in polyacetal, into a polymer by anionic polymerization in cooling after heating and melting, such as molding, and immobilization of the polymer onto the polyacetal resin composition, thereby resulting in a reduction in generation of formaldehyde, acetaldehyde, acrolein, and the like. The mechanism of the effect of the present embodiment, however, is not limited thereto.

In the present embodiment, R2 in the quaternary ammonium compound (A) has 2 to 10 carbon atoms and 2 to 5 oxygen atoms. The number of carbon atoms and the number of oxygen atoms within such ranges allow the quaternary ammonium compound (A) to efficiently remain in polyacetal even through heating, and thereby enabling to reduce the generation of a volatile organic substance in cooling after heating and melting.

While the larger the number of carbon atoms and the number of oxygen atoms in R2 is the better from the viewpoint of suppression of generation of a volatile organic substance, when the numbers are excessively large, coloration of a molded article including the compound is caused. Accordingly, the numbers are preferably proper values in terms of the balance between suppression of generation of a volatile organic substance and prevention of coloration in consideration of the temperature, the time, and the like of the heating treatment. Specifically, preferably R2 has 2 to 6 carbon atoms and 2 to 3 oxygen atoms, and particularly preferably R2 has 4 carbon atoms and 2 oxygen atoms.

EXAMPLES

Hereinafter, the present invention will be described with reference to specific Examples and Comparative Examples thereof, but the present invention is not intended to be limited to the following Examples.

The methods for evaluating various properties, adopted in Examples and Comparative Examples, will be described.
<Quantitative Determination of Formaldehyde, Acetaldehyde, and Acrolein>

1. Pellet (before Heating and Melting)

(1-a)
A 10-L Tedlar (registered trademark) bag having a valve was charged with 20.00 g of a polyacetal resin composition pellet and sealed, and sufficiently purged with nitrogen. Thereafter, nitrogen in the bag was fully discharged, and thereafter 5.00 L of nitrogen was encapsulated in the Tedlar (registered trademark) bag.

Thereafter, the Tedlar (registered trademark) bag was loaded in an oven having a sampling port in communication with the outside, on the upper portion of the inside, and the Tedlar (registered trademark) bag was connected to the sampling port, and then left to stand at 90° C. for 2 hours.

Thereafter, a DNPH (2,4-dinitrophenylhydrazine) cartridge was connected to the outside of the sampling port to which the Tedlar (registered trademark) bag was connected, the valve of the Tedlar (registered trademark) bag was opened, and 4.00 L of gas generated from the polyacetal composition was allowed to pass through the DNPH cartridge.

Five mL of acetonitrile was allowed to flow through the DNPH cartridge at a constant rate, and formaldehyde and acetaldehyde were recovered in a 10-mL measuring flask.

Thereafter, the resultant was diluted with water to 10 mL in total, and the dilution was sufficiently mixed.

This mixed liquid was dispensed in a vial container, and subjected to quantitative determination under conditions of a flow rate of 1 mL/min and a column temperature of 40° C. by use of a DNPH standard liquid as a standard liquid and water/acetonitrile (52/48) as a separation liquid with HPLC manufactured by Shimadzu Corporation, and the amount of formaldehyde generated per mass of the polyacetal resin composition pellet was measured by ppm.
(1-b)
A 10-L Tedlar (registered trademark) bag having a valve was charged with 20.00 g of a polyacetal resin composition pellet and sealed, and sufficiently purged with nitrogen. Thereafter, nitrogen in the bag was fully discharged, and thereafter 5.00 L of nitrogen was encapsulated in the Tedlar (registered trademark) bag. Two of such bags were prepared.

Thereafter, the Tedlar (registered trademark) bags were loaded in an oven having two sampling ports in communication with the outside, on the upper portion of the inside, and the Tedlar (registered trademark) bags were connected to the sampling ports, and then left to stand at 90° C. for 2 hours.

Thereafter, a DNPH (2,4-dinitrophenylhydrazine) cartridge was connected to the outside of the sampling port to which one of the Tedlar (registered trademark) bags was connected, the valve of the Tedlar (registered trademark) bag was opened, and 4.00 L of gas generated from the polyacetal resin composition was allowed to pass through the DNPH cartridge.

Five mL of acetonitrile was allowed to flow through the DNPH cartridge at a constant rate, and formaldehyde and acetaldehyde were recovered in a 10-mL measuring flask.

Thereafter, the resultant was diluted with water to 10 mL in total, and the dilution was sufficiently mixed.

This mixed liquid was dispensed in a vial container, and subjected to quantitative determination under conditions of a flow rate of 1 mL/min and a column temperature of 40° C. by use of a DNPH standard liquid as a standard liquid and water/acetonitrile (52/48) as a separation liquid with HPLC manufactured by Shimadzu Corporation, and the amounts of formaldehyde and acetaldehyde generated per mass of the polyacetal resin composition pellet were measured by ppm.

The measurement upper limit was 15 ppm or less, and a value more than the measurement upper limit was defined as O.D. (unmeasurable) and a value of less than 0.01 ppm was defined as N.D.

A CNET (O-(4-cyano-2-ethoxybenzyl)hydroxylamine) cartridge was connected to the outside of the sampling port to which the other Tedlar (registered trademark) bag was connected, the valve of the Tedlar (registered trademark) bag was opened, and 4.00 L of gas generated from the polyacetal resin composition was allowed to pass through the CNET cartridge.

Five mL of acetonitrile was allowed to flow through the CNET cartridge at a constant rate, and acrolein was recovered in a 10-mL measuring flask.

Thereafter, the resultant was diluted with water to 10 mL in total, and the dilution was sufficiently mixed.

This mixed liquid was dispensed in a vial container, and subjected to quantitative determination under conditions of a flow rate of 1 mL/min and a column temperature of 40° C. by use of a CNET standard liquid as a standard liquid and water/acetonitrile (40/60) as a separation liquid with HPLC manufactured by Shimadzu Corporation, and the amount of acrolein generated per mass of the polyacetal resin composition pellet was measured by ppb.

The measurement upper limit was 30 ppb or less, and a value more than 20 ppb was defined as O.D.

2. Molded Piece (after Heating and Melting)

(2-a)
An IS-100GN injection molding machine manufactured by Toshiba Corporation was used to subject the polyacetal resin composition pellet to heating and melting of the composition under conditions of a cylinder temperature of 200° C., an injection pressure of 60 MPa, an injection time of 15 seconds, a cooling time of 20 seconds, and a molding temperature of 80° C., thereby producing a molded piece having a planar shape and having a dimension of 130 mm×110 mm×3 mm.

The molded piece was left to stand in a constant temperature room kept at 23° C. and at a humidity of 50%, for 24 hours, and thereafter loaded in an aluminum bag and packed. The bag was opened after 14 days of molding, and one of the molded piece was loaded in a 10-L Tedlar (registered trademark) bag having a valve and sealed, and sufficiently purged with nitrogen. Thereafter, nitrogen in the bag was fully discharged, and thereafter 5.00 L of nitrogen was encapsulated in the Tedlar (registered trademark) bag. Two of such bags were prepared.

Thereafter, the Tedlar (registered trademark) bags were loaded in an oven having two sampling ports in communication with the outside, on the upper portion of the inside, and the Tedlar (registered trademark) bags were connected to the sampling ports, and then left to stand at 80° C. for 2 hours.

Thereafter, one of the Tedlar (registered trademark) bags was used to quantitatively determine the amounts of formaldehyde and acetaldehyde in the same manner as in case (1-a) of the pellet.

A CNET (O-(4-cyano-2-ethoxybenzyl)hydroxylamine) cartridge was connected to the outside of the sampling port to which the other Tedlar (registered trademark) bag was connected, the valve of the Tedlar (registered trademark) bag was opened, and 4.00 L of gas generated from the polyacetal composition was allowed to pass through the CNET cartridge.

Five mL of acetonitrile was allowed to flow through the CNET cartridge at a constant rate, and acrolein was recovered in a 10-mL measuring flask.

Thereafter, the resultant was diluted with water to 10 mL in total, and the dilution was sufficiently mixed.

This mixed liquid was dispensed in a vial container, and subjected to quantitative determination under conditions of a flow rate of 1 mL/min and a column temperature of 40° C. by use of a CNET standard liquid as a standard liquid and water/acetonitrile (40/60) as a separation liquid with HPLC manufactured by Shimadzu Corporation, and the amount of acrolein generated per mass of the polyacetal resin composition was measured by ppb.

(2-b)
An IS-100GN injection molding machine manufactured by Toshiba Corporation was used to subject the polyacetal resin composition pellet to heating and melting of the resin composition under conditions of a cylinder temperature of 200° C., an injection pressure of 60 MPa, an injection time of 15 seconds, a cooling time of 20 seconds, and a molding temperature of 80° C., thereby producing a molded piece having a planar shape and having a dimension of 130 mm×110 mm×3 mm.

The molded piece was left to stand in a constant temperature room kept at 23° C. and at a humidity of 50%, for 24 hours, and thereafter loaded in an aluminum bag and packed. The bag was opened after 14 days of molding, and one of the molded piece was loaded in a 10-L Tedlar (registered trademark) bag having a valve and sealed, and sufficiently purged with nitrogen. Thereafter, nitrogen in the bag was fully discharged, and thereafter 5.00 L of nitrogen was encapsulated in the Tedlar (registered trademark) bag. Two of such bags were prepared.

Thereafter, the Tedlar (registered trademark) bag was loaded in an oven having a sampling port in communication with the outside, on the upper portion of the inside, and the Tedlar (registered trademark) bag was connected to the sampling port, and then left to stand at 80° C. for 2 hours.

The same manner as in case (1-b) of the pellet was made with respect to the subsequent operations, thereby quantitatively determining the amounts of formaldehyde, acetaldehyde, and acrolein.

<Color Tone Properties>

1. Pellet (before Heating and Melting)

The yellowness (b value) was measured in a light source of a halogen lamp by use of a colorimeter ZE 2000 manufactured by Nippon Denshoku Industries Co., Ltd., by using about 20 g of the polyacetal resin composition pellet.

A case where the b value was −0.8 or less was determined as being almost favorable, and a case where the b value was −1.6 or less was determined as being favorable.

2. Molded Piece (after Heating and Melting)

(2-a)
An IS-100GN injection molding machine manufactured by Toshiba Corporation was used to produce a test piece having a planar shape and having a dimension of 40 mm×60 mm×3 mm, under conditions of a cylinder temperature of 200° C., an injection pressure of 60 MPa, an injection time of 15 seconds, a cooling time of 20 seconds, and a molding temperature of 80° C.

Molding was made to provide 1002 of such test pieces, the $1001^{st}$ test piece and the $1002^{nd}$ test piece were stacked, and the yellowness (b value) was measured in a D65 light source by use of a handy color meter (CR-200) manufactured by Konica Minolta, Inc. A case where the b value was −0.8 or less was determined as being almost favorable, and a case where the b value was −1.6 or less was determined as being favorable.

(2-b)
An IS-100GN injection molding machine manufactured by Toshiba Corporation was used to produce a test piece having a planar shape and having a dimension of 130 mm×110 mm×3 mm, from the polyacetal resin composition pellet, under conditions of a cylinder temperature of 200° C., an injection pressure of 60 MPa, an injection time of 15 seconds, a cooling time of 20 seconds, and a molding temperature of 80° C.

Two of such test pieces were stacked, and the yellowness (b value) was measured in a D65 light source by use of a handy color meter (CR-200) manufactured by Konica Minolta, Inc.

A case where the b value was −0.8 or less was determined as being almost favorable, and a case where the b value was −1.6 or less was determined as being favorable.

<Evaluation (Visual Observation in MD) of Mold Contamination Properties in Molding>

An IS-100GN injection molding machine manufactured by Toshiba Corporation was used to produce a test piece having a planar shape and having a dimension of 40 mm×60 mm×3 mm, under conditions of a cylinder temperature of 200° C., an injection pressure of 60 MPa, an injection time of 15 seconds, a cooling time of 20 seconds, and a molding temperature of 80° C.

After molding was made to provide 1000 of the test pieces, the attachment of formaldehyde to the mold (mold deposit) was visually observed. A case where the mold was contaminated was rated as "x", and a case where the mold was not contaminated was rated as "○".

<Evaluation of Color Tone of Quaternary Ammonium Compound>

In an aluminum vessel having a diameter of 10 cm and a height of 1 cm was weighed 10 cc of a solution of the quaternary ammonium compound (A) in water, the aluminum vessel was placed on a hot plate set at 150° C., and additional 10 cc of the solution was weight and then added at the same time as the loss of the water content. Thereafter, the color of the residue on the bottom of the aluminum vessel was visually observed at the same time as the loss of the water content, and the color was evaluated.

A color close to brown was rated as "×", a color closer to light yellow to colorless was rated as "○", and a color therebetween was rated as "Δ".

Such evaluation was performed with respect to the aqueous solution of each quaternary ammonium compound (A) obtained in Production Examples 1, 7, 8, and 12 to 19.

<Production of Quaternary Ammonium Compound (A) Represented by Formula (1)>

Deionized water was used as the water in all Production Examples 1 to 11.

Production Example 1

Into a sealable pressure-resistant vessel having an inner volume of 60 ml were introduced 14.1 g of 2-(2-hydroxyethoxy)ethyl acetate, 5.6 g of trimethylamine, 15.0 g of methanol, and 0.1 g of water, and the resulting mixture was heated to 120° C. with stirring in a shaking machine. Thereafter, the reaction was allowed to run for 6 hours, and then cooled to provide a content. The content was subjected to analysis, and as a result, 2-(2-hydroxyethoxy)ethyl-N,N,N-trimethylethane-1-ammonium acetate was obtained at a yield of 95%.

After 15 g of water was loaded to 30 g of the solution, the mixture was concentrated to 30 g by an evaporator at 80° C., and diluted with water to 60 g in total. The resultant was again concentrated to 30 g, and then diluted with water to 60 g in total. The operation was repeated ten times for concentration to 15 g, and then dilution with water was made to 80 g in total. This liquid was defined as A-1.

The structural formula (R1, R2 and X) of the quaternary ammonium compound (A) in liquid A-1, confirmed by NMR, was as shown in Table 1, and the concentration was about 20% by mass.

Production Example 2

The same manner as in Production Example 1 was performed except that 18.2 g of 2-(2-(2-hydroxyethoxy)ethoxy)ethyl acetate was used instead of 14.1 g of 2-(2-hydroxyethoxy)ethyl acetate. This liquid was defined as A-2.

The structural formula (R1, R2 and X) of the quaternary ammonium compound (A) in liquid A-2, confirmed by NMR, was as shown in Table 1, and the concentration was about 22% by mass.

Production Example 3

The same manner as in Production Example 1 was performed except that 7.8 g of triethylamine was used instead of 5.6 g of trimethylamine, and 11.4 g of 2-(2-hydroxyethoxy) ethyl acetate was used. This liquid was defined as A-3.

The structural formula (R1, R2 and X) of the quaternary ammonium compound (A) in liquid A-3, confirmed by NMR, was as shown in Table 1, and the concentration was about 20% by mass.

Production Example 4

The same manner as in Production Example 1 was performed except that 7.8 g of triethylamine was used instead of 5.6 g of trimethylamine, and 14.8 g of 2-(2-(2-hydroxyethoxy)ethoxy)ethyl acetate was used instead of 2-(2-hydroxyethoxy)ethyl acetate. This liquid was defined as A-4.

The structural formula (R1, R2 and X) of the quaternary ammonium compound (A) in liquid A-4, confirmed by NMR, was as shown in Table 1, and the concentration was about 21% by mass.

Production Example 5

The same manner as in Production Example 1 was performed except that 9.4 g of 2-[2-(dimethylamino)ethoxy]ethanol was used instead of 5.6 g of trimethylamine, and 10.5 g of 2-(2-hydroxyethoxy)ethyl acetate was used. This liquid was defined as A-5.

The structural formula (R1, R2 and X) of the quaternary ammonium compound (A) in liquid A-5, confirmed by NMR, was as shown in Table 1, and the concentration was about 20% by mass.

Production Example 6

Into a 10-ml microwave reaction tube were loaded 5.0 g of trimethylamine and 2.63 g of 2-(2-chloroethoxy)ethanol, and the resultant was stirred at 150° C. for 1 hour while being irradiated with microwaves. After completion of the reaction, the reaction liquid was dried under reduced pressure to provide a powder crystal. The reaction liquid after completion of the reaction was analyzed by HPLC, and as a result, it was confirmed that the reaction rate was 100%. After dichloroethane was added to the resulting powder crystal, and stirred, the resultant was filtered to provide a crystal. The operation was repeated three times, and drying was made under reduced pressure, thereby providing 2.58 g of a powder crystal.

To 1 kg of an ethanol solution where 100 g of sodium hydroxide was dissolved at 40° C. was added 5.62 g of the powder, and sodium chloride was separated by filtration to collect a filtrate. After 6.46 g of an aqueous formic acid solution including formic acid/water at a mass ratio of 10/90 was added to the filtrate, the resultant was concentrated to 5 g by an evaporator, and 10 g of water was added thereto.

After the concentration and the addition of 10 g of water were repeated three times, the resultant whose final amount was 15 g was defined as A-6.

The structural formula (R1, R2 and X) of the quaternary ammonium compound (A) in liquid A-6, confirmed by NMR, was as shown in Table 1, and the concentration was about 17% by mass.

Production Example 7

The same manner as in Production Example 6 except that 4.5 g of trimethylamine was used and 3.21 g of 2-[2-(2-chloroethoxy)ethoxy]ethanol was used instead of 2-(2-chloroethoxy)ethanol, thereby providing 3.10 g of a powder crystal.

The powder was used with 5.44 g of the ethanol solution of sodium hydroxide and 6.26 g of an aqueous formic acid solution, used in Production Example 6, to perform separation by filtration of sodium chloride and concentration in the same manner as in Production Example 6, and the resultant whose final amount was 15 g was defined as A-7.

The structural formula (R1, R2 and X) of the quaternary ammonium compound (A) in liquid A-7, confirmed by NMR, was as shown in Table 1, and the concentration was about 20% by mass.

Production Example 8

The same manner as in Production Example 6 except that 5.8 g of triethylamine was used instead of trimethylamine and 1.79 g of 2-(2-chloroethoxy)ethanol was used, thereby providing 1.76 g of a powder crystal.

The powder was used with 3.11 g of the ethanol solution of sodium hydroxide and 3.58 g of an aqueous formic acid solution, used in Production Example 6, to perform separation by filtration of sodium chloride and concentration in the same manner as in Production Example 6, and the resultant whose final amount was 15 g was defined as A-8.

The structural formula (R1, R2 and X) of the quaternary ammonium compound (A) in liquid A-8, confirmed by NMR, was as shown in Table 1, and the concentration was about 12% by mass.

Production Example 9

The same manner as in Production Example 6 except that 5.4 g of triethylamine was used instead of trimethylamine and 2.25 g of 2-[2-(2-chloroethoxy)ethoxy]ethanol was used instead of 2-(2-chloroethoxy)ethanol, thereby providing 2.18 g of a powder crystal.

The powder was used with 3.24 g of the ethanol solution of sodium hydroxide and 3.72 g of an aqueous formic acid solution, used in Production Example 6, to perform separation by filtration of sodium chloride and concentration in the same manner as in Production Example 6, and the resultant whose final amount was 15 g was defined as A-9.

The structural formula (R1, R2 and X) of the quaternary ammonium compound (A) in liquid A-9, confirmed by NMR, was as shown in Table 1, and the concentration was about 14% by mass.

Production Example 10

The same manner as in Production Example 6 except that 4.0 g of trimethylamine was used and 3.60 g of 2-[2-[2-(2-chloroethoxy)ethoxy]ethoxy]ethanol was used instead of 2-(2-chloroethoxy)ethanol, thereby providing 3.41 g of a powder crystal.

The powder was used with 5.02 g of the ethanol solution of sodium hydroxide and 5.77 g of an aqueous formic acid solution, used in Production Example 6, to perform separation by filtration of sodium chloride and concentration in the same manner as in Production Example 6, and the resultant whose final amount was 15 g was defined as A-10.

The structural formula (R1, R2 and X) of the quaternary ammonium compound (A) in liquid A-10, confirmed by NMR, was as shown in Table 1, and the concentration was about 22% by mass.

Production Example 11

The same manner as in Production Example 6 except that 5.0 g of triethylamine was used instead of trimethylamine and 2.63 g of 2-[2-[2-(2-chloroethoxy)ethoxy]ethoxy]ethanol was used instead of 2-(2-chloroethoxy)ethanol, thereby providing 2.50 g of a powder crystal.

The powder was used with 3.19 g of the ethanol solution of sodium hydroxide and 3.67 g of an aqueous formic acid solution, used in Production Example 6, to perform separation by filtration of sodium chloride and concentration in the same manner as in Production Example 6, and the resultant whose final amount was 15 g was defined as A-11.

The structural formula (R1, R2 and X) of the quaternary ammonium compound (A) in liquid A-11, confirmed by NMR, was as shown in Table 1, and the concentration was about 16% by mass.

Production Example 12

To aqueous solution A-1 obtained in Production Example 1 was added 0.05 ppm by mass of magnesium hydroxide relative to the quaternary ammonium compound. The resultant was defined as A-12.

Production Example 13

To aqueous solution A-1 obtained in Production Example 1 was added 0.1 ppm by mass of magnesium hydroxide relative to the quaternary ammonium compound. The resultant was defined as A-13.

Production Example 14

To aqueous solution A-1 obtained in Production Example 1 was added 0.7 ppm by mass of magnesium hydroxide relative to the quaternary ammonium compound. The resultant was defined as A-14.

Production Example 15

To aqueous solution A-1 obtained in Production Example 1 was added 0.4 ppm by mass of sodium hydroxide relative to the quaternary ammonium compound. The resultant was defined as A-15.

Production Example 16

To aqueous solution A-1 obtained in Production Example 1 was added 1.6 ppm by mass of magnesium hydroxide relative to the quaternary ammonium compound. The resultant was defined as A-16.

Production Example 17

To aqueous solution A-1 obtained in Production Example 1 was added 0.28 ppm by mass of calcium hydroxide relative to the quaternary ammonium compound. The resultant was defined as A-17.

Production Example 18

To aqueous solution A-7 obtained in Production Example 7 was added 0.28 ppm by mass of magnesium hydroxide relative to the quaternary ammonium compound. The resultant was defined as A-18.

Production Example 19

To aqueous solution A-8 obtained in Production Example 8 was added 10.0 ppm by mass of sodium hydroxide relative to the quaternary ammonium compound. The resultant was defined as A-19.

Production Example 20

To aqueous solution A-1 obtained in Production Example 1 was added 8.0 ppm by mass of potassium hydroxide relative to the quaternary ammonium compound. The resultant was defined as A-20.

In the Production Example, such an operation was repeated depending on the required amount.

TABLE 1

| | R1 | R1 | R1/R2 | R2 | X |
|---|---|---|---|---|---|
| Production Example 1 | —CH3 | —CH3 | —CH3 | —C2H4OC2H4OH | acetate |
| Production Example 2 | —CH3 | —CH3 | —CH3 | —C2H4OC2H4OC2H4OH | acetate |
| Production Example 3 | —C2H5 | —C2H5 | —C2H5 | —C2H4OC2H4OH | acetate |
| Production Example 4 | —C2H5 | —C2H5 | —C2H5 | —C2H4OC2H4OC2H4OH | acetate |
| Production Example 5 | —CH3 | —CH3 | —C2H4OC2H4OH | —C2H4OC2H4OH | acetate |
| Production Example 6 | —CH3 | —CH3 | —CH3 | —C2H4OC2H4OH | formate |
| Production Example 7 | —CH3 | —CH3 | —CH3 | —C2H4OC2H4OC2H4OH | formate |
| Production Example 8 | —C2H5 | —C2H5 | —C2H5 | —C2H4OC2H4OH | formate |
| Production Example 9 | —C2H5 | —C2H5 | —C2H5 | —C2H4OC2H4OC2H4OH | formate |
| Production Example 10 | —CH3 | —CH3 | —CH3 | —C2H4OC2H4OC2H4OC2H4OH | formate |
| Production Example 11 | —C2H5 | —C2H5 | —C2H5 | —C2H4OC2H4OC2H4OC2H4OH | formate |

<(Poly)alkylene Glycol Represented by Formula (2)>

B-1: ethylene glycol (manufactured by FUJIFILM Wako Pure Chemical Corporation)

B-2: diethylene glycol (manufactured by FUJIFILM Wako Pure Chemical Corporation), and B-3: polyethylene glycol 600 (manufactured by FUJIFILM Wako Pure Chemical Corporation) were used.

<Quaternary Ammonium Compound (C) Represented by Formula (3)>

C-1: choline acetic acid salt (manufactured by Sigma Aldrich), and

C-2: choline hydroxide (manufactured by Tama Chemicals Co., Ltd.) were used.

Example a

1. Preparation of Quaternary Ammonium Composition

Preparation Example 1

B-1 was mixed with aqueous solution A-1 produced in Production Example 1, in an amount of 5% by mass relative to A-1, and the mixture was well stirred. Thereafter, the mixture was loaded in a 100-ml aluminum round can, the lid was closed, and heat retention was made at 60° C. for 6 months, thereby providing a quaternary ammonium composition. The resulting quaternary ammonium composition was defined as Z-1.

Preparation Examples 2 to 35

Each quaternary ammonium composition whose chemical composition was as shown in Table 2 was prepared in the same manner as in Preparation Example 1. In Table 2, (C), if used, was described with respect to the type and the amount (% by mass) relative to (A), and (B), if used, was described with respect to the amount (% by mass) based on the total amount of the quaternary ammonium composition (total amount of (A), (B) and (C)).

Preparation Example 36

A quaternary ammonium composition was obtained in the same manner as in Preparation Example 6 except that the heat retention time at 60° C. was changed to 1 day. The resulting quaternary ammonium composition was defined as Z-36.

Preparation Example 37

Aqueous solution A-1 produced in Production Example 1 was loaded in a 100-ml aluminum round can, the lid was closed, and heat retention was made at 60° C. for 6 months, thereby providing a quaternary ammonium composition. The resulting quaternary ammonium composition was defined as Z-1'.

Preparation Example 38

Aqueous solution A-6 produced in Production Example 6 was loaded in a 100-ml aluminum round can, the lid was closed, and heat retention was made at 60° C. for 6 months, thereby providing a quaternary ammonium composition. The resulting quaternary ammonium composition was defined as Z-6'.

Preparation Example 39

Aqueous solution A-3 produced in Production Example 3 was loaded in a 100-ml aluminum round can, the lid was closed, and heat retention was made at 60° C. for 6 months, thereby providing a quaternary ammonium composition. The resulting quaternary ammonium composition was defined as Z-3'.

Preparation Example 40

Aqueous solution A-6 produced in Production Example 6 was loaded in a 100-ml aluminum round can, the lid was closed, and heat retention was made at 60° C. for 1 day, thereby providing a quaternary ammonium composition. The resulting quaternary ammonium composition was defined as Z-36'.

2. Method for Producing Crude Polyacetal

The temperature of a twin-paddle type continuous polymerization reactor equipped with a jacket capable of allowing a heat medium to pass (manufactured by KURIMOTO, LTD., diameter: 2B (2 inches), L (the distance from the raw material feed port to the discharge port of the polymerization reactor)/D (the inner diameter of the polymerization reactor)= 14.8) was adjusted to 80° C.

Next, boron trifluoride-di-n-butyl etherate as a polymerization catalyst at 0.15 g/hr, methylal as a low-molecular weight acetal at 2.30 g/hr, cyclohexane at 100.50 g/hr, and 1,3-dioxolane at 110.9 g/hr and trioxane at 3300 g/hr as a cyclic ether and/or a cyclic formal were continuously fed to the polymerization reactor through a pipe to perform polymerization, thereby providing crude polyacetal copolymer (aP-1).

Crude polyacetal copolymer (aP-1) was charged in an aqueous 0.1% by mass triethylamine solution, and the catalyst was deactivated. Thereafter, the resultant was dried at 120° C. after filtration/washing, thereby providing crude polyacetal copolymer (aP-2).

3. Examples/Comparative Examples

Examples a1 to a36

Crude polyacetal copolymer (aP-1) was charged in an aqueous 0.5% triethylamine solution, and the polymerization catalyst was deactivated. Thereafter, filtration and washing were performed, the quaternary ammonium composition produced in each of Preparation Examples was added in an amount based on 100 parts by mass of the resulting crude polyacetal copolymer (aP-1) so that the concentration n of nitrogen was as shown in Table 3, and the resultant was uniformly mixed and then dried at 130° C.

Added was 0.2 parts by mass of 2,2'-methylenebis-(4-methyl-t-butylphenol) as an antioxidant based on 100 parts by mass of the crude polyacetal copolymer composition containing the quaternary ammonium composition obtained in each of Preparation Examples, and fed to a twin-screw type extruder equipped with a vent.

Water and triethylamine were added to the crude polyacetal copolymer composition molten in the extruder in amounts of 3% by mass and 0.5% by mass (both were contents relative to the quaternary ammonium composition), respectively, and an unstable terminal portion of the crude polyacetal copolymer was decomposed at a preset temperature of the extruder, of 210° C., for a retention time in the extruder, of 5 minutes. The polyacetal copolymer from which an unstable terminal portion was decomposed was subjected to degassing under a condition of a vent vacuum degree of 20 Torr, and extruded as a strand from a die section of the extruder, and pelletized.

Examples a37 to a40

The same manner as in Examples a1, a6, a3, and a36 was performed except that Z-1', 6', 3', or 36' was used as the quaternary ammonium composition, namely, no (poly)alkylene glycol (B) was used.

Comparative Example a1

The same manner as in Example a1 was performed except that neither the quaternary ammonium compound (A) nor the (poly)alkylene glycol (B) was used.

The types of the quaternary ammonium compound (A), the (poly)alkylene glycol (B) and the quaternary ammonium compound (C) used, the amount of the quaternary ammonium compound (A) used (content based on the total of the polyacetal copolymer and the quaternary ammonium composition) (the concentration n of nitrogen derived from the quaternary ammonium compound (A)), the amount of formaldehyde (FA) generated from the pellet (from 1-a), and the amounts of formaldehyde (FA), acetaldehyde (AA) and acrolein (AL) generated from the molded piece (from 2-a), as well as the evaluation results of the color tone of the pellet, the color tone of the molded piece (from 2-a), and mold contamination properties (visual observation in MD) are collectively shown in Table 3.

TABLE 2

| | Sample name | Type of (A) | Type of (B) | Formulation conditions of quaternary ammonium composition | | | |
|---|---|---|---|---|---|---|---|
| | | | | Amount of (B) added (% by mass relative to total quaternary ammonium) | Type of (C) | Amount of (C) added (% by mass relative to (A)) | Heat retention time at 60° C. |
| Preparation Example 1 | Z-1 | A-1 | B-1 | 5 | — | — | 6 months |
| Preparation Example 2 | Z-2 | A-2 | B-1 | 5 | — | — | 6 months |
| Preparation Example 3 | Z-3 | A-3 | B-1 | 5 | — | — | 6 months |
| Preparation Example 4 | Z-4 | A-4 | B-1 | 5 | — | — | 6 months |
| Preparation Example 5 | Z-5 | A-5 | B-1 | 5 | — | — | 6 months |
| Preparation Example 6 | Z-6 | A-6 | B-1 | 10 | — | — | 6 months |
| Preparation Example 7 | Z-7 | A-7 | B-1 | 10 | — | — | 6 months |
| Preparation Example 8 | Z-8 | A-8 | B-1 | 10 | — | — | 6 months |
| Preparation Example 9 | Z-9 | A-9 | B-1 | 10 | — | — | 6 months |
| Preparation Example 10 | Z-10 | A-10 | B-1 | 10 | — | — | 6 months |
| Preparation Example 11 | Z-11 | A-11 | B-1 | 10 | — | — | 6 months |

TABLE 2-continued

| | | | | Formulation conditions of quaternary ammonium composition | | | |
|---|---|---|---|---|---|---|---|
| | Sample name | Type of (A) | Type of (B) | Amount of (B) added (% by mass relative to total quaternary ammonium) | Type of (C) | Amount of (C) added (% by mass relative to (A)) | Heat retention time at 60° C. |
| Preparation Example 12 | Z-12 | A-3 | B-1 | 25 | — | — | 6 months |
| Preparation Example 13 | 2-13 | A-3 | B-1 | 35 | — | — | 6 months |
| Preparation Example 14 | Z-14 | A-3 | B-1 | 90 | — | — | 6 months |
| Preparation Example 15 | Z-15 | A-3 | B-2 | 10 | — | — | 6 months |
| Preparation Example 16 | Z-16 | A-3 | B-2 | 25 | — | — | 6 months |
| Preparation Example 17 | Z-17 | A-3 | B-2 | 35 | — | — | 6 months |
| Preparation Example 18 | Z-18 | A-3 | B-2 | 90 | — | — | 6 months |
| Preparation Example 19 | Z-19 | A-6 | B-2 | 20 | — | — | 6 months |
| Preparation Example 20 | Z-20 | A-8 | B-2 | 20 | — | — | 6 months |
| Preparation Example 21 | Z-21 | A-3 | B-3 | 5 | — | — | 6 months |
| Preparation Example 22 | Z-22 | A-3 | B-3 | 10 | — | — | 6 months |
| Preparation Example 23 | Z-23 | A-3 | B-3 | 15 | — | — | 6 months |
| Preparation Example 24 | Z-24 | A-6 | B-3 | 10 | — | — | 6 months |
| Preparation Example 25 | Z-25 | A-8 | B-3 | 10 | — | — | 6 months |
| Preparation Example 26 | Z-26 | A-3 | B-1 | 10 | C-1 | 5 | 6 months |
| Preparation Example 27 | Z-27 | A-3 | B-1 | 10 | C-1 | 10 | 6 months |
| Preparation Example 28 | Z-28 | A-3 | B-1 | 10 | C-1 | 15 | 6 months |
| Preparation Example 29 | Z-29 | A-6 | B-1 | 10 | C-1 | 10 | 6 months |
| Preparation Example 30 | Z-30 | A-8 | B-1 | 10 | C-1 | 10 | 6 months |
| Preparation Example 31 | Z-31 | A-3 | B-1 | 10 | C-2 | 5 | 6 months |
| Preparation Example 32 | Z-32 | A-3 | B-1 | 10 | C-2 | 10 | 6 months |
| Preparation Example 33 | Z-33 | A-3 | B-1 | 10 | C-2 | 15 | 6 months |
| Preparation Example 34 | Z-34 | A-6 | B-1 | 10 | C-2 | 10 | 6 months |
| Preparation Example 35 | Z-35 | A-8 | B-1 | 10 | C-2 | 10 | 6 months |
| Preparation Example 36 | Z-36 | A-6 | B-1 | 10 | — | — | 1 day |
| Preparation Example 37 | Z-1' | A-1 | — | — | — | — | 6 months |
| Preparation Example 38 | Z-6' | A-6 | — | — | — | — | 6 months |
| Preparation Example 39 | Z-3' | A-3 | — | — | — | — | 6 months |
| Preparation Example 40 | Z-36' | A-6 | — | — | — | — | 1 day |

TABLE 3

| | Type of quaternary ammonium composition | Type of (A) | Amount of (A) used (in terms of amount of nitrogen) [ppm] | Type of (B) | Type of (C) | Pellet FA [ppm] | Pellet Color tone | Molded piece FA [ppm] | Molded piece AA [ppm] | Molded piece AL [ppb] | Color tone (b value) | Visual observation in MD |
|---|---|---|---|---|---|---|---|---|---|---|---|---|
| Example a1 | Z-1 | A-1 | 10 | B-1 | — | 0.75 | −1.9 | 1.51 | 0.03 | 7.1 | −1.9 | ○ |
| Example a2 | Z-2 | A-2 | 10 | B-1 | — | 0.75 | −1.8 | 1.50 | 0.03 | 7.1 | −1.8 | ○ |
| Example a3 | Z-3 | A-3 | 10 | B-1 | — | 0.74 | −1.8 | 1.49 | 0.04 | 6.9 | −1.8 | ○ |
| Example a4 | Z-4 | A-4 | 10 | B-1 | — | 0.73 | −1.8 | 1.48 | 0.04 | 5.5 | −1.8 | ○ |
| Example a5 | Z-5 | A-5 | 10 | B-1 | — | 0.68 | −1.9 | 1.49 | 0.03 | 5.4 | −1.8 | ○ |
| Example a6 | Z-6 | A-6 | 14 | B-1 | — | 0.74 | −1.9 | 1.29 | 0.02 | 4.8 | −1.8 | ○ |
| Example a7 | Z-7 | A-7 | 14 | B-1 | — | 0.78 | −1.9 | 1.21 | 0.02 | 4.2 | −1.8 | ○ |
| Example a8 | Z-8 | A-8 | 14 | B-1 | — | 0.77 | −1.9 | 0.93 | 0.02 | 3.9 | −1.8 | ○ |
| Example a9 | Z-9 | A-9 | 14 | B-1 | — | 0.77 | −1.8 | 0.98 | 0.02 | 3.8 | −1.8 | ○ |
| Example a10 | Z-10 | A-10 | 14 | B-1 | — | 0.84 | −1.8 | 1.68 | 0.05 | 5.6 | −1.3 | ○ |
| Example a11 | Z-11 | A-11 | 14 | B-1 | — | 0.86 | −1.9 | 1.71 | 0.05 | 7.1 | −1.3 | ○ |
| Example a12 | Z-12 | A-3 | 14 | B-1 | — | 0.74 | −1.9 | 1.28 | 0.03 | 7.4 | −1.8 | ○ |
| Example a13 | Z-13 | A-3 | 14 | B-1 | — | 0.74 | −1.9 | 1.41 | 0.06 | 7.3 | −1.8 | ○ |
| Example a14 | Z-14 | A-3 | 14 | B-1 | — | 1.29 | −1.8 | 4.74 | 1.08 | 7.1 | −1.7 | ○ |
| Example a15 | Z-15 | A-3 | 14 | B-2 | — | 0.74 | −1.9 | 1.61 | 0.04 | 7.0 | −1.8 | ○ |
| Example a16 | Z-16 | A-3 | 14 | B-2 | — | 0.74 | −1.9 | 1.19 | 0.02 | 7.4 | −1.8 | ○ |
| Example a17 | Z-17 | A-3 | 14 | B-2 | — | 0.74 | −1.9 | 1.31 | 0.06 | 7.3 | −1.8 | ○ |
| Example a18 | Z-18 | A-3 | 14 | B-2 | — | 1.26 | −1.8 | 4.84 | 1.12 | 7.1 | −1.7 | ○ |
| Example a19 | Z-19 | A-6 | 14 | B-2 | — | 0.74 | −1.9 | 0.98 | 0.02 | 3.8 | −1.8 | ○ |
| Example a20 | Z-20 | A-8 | 14 | B-2 | — | 0.68 | −1.9 | 0.93 | 0.02 | 3.9 | −1.8 | ○ |
| Example a21 | Z-21 | A-3 | 14 | B-3 | — | 0.77 | −1.7 | 2.61 | 0.05 | 7.4 | −1.6 | ○ |
| Example a22 | Z-22 | A-3 | 14 | B-3 | — | 0.78 | −1.8 | 2.51 | 0.05 | 7.3 | −1.7 | ○ |
| Example a23 | Z-23 | A-3 | 14 | B-3 | — | 0.81 | −1.7 | 2.41 | 0.05 | 6.5 | −1.6 | ○ |
| Example a24 | Z-24 | A-6 | 14 | B-3 | — | 0.74 | −1.7 | 2.65 | 0.05 | 7.4 | −1.6 | ○ |
| Example a25 | Z-25 | A-8 | 14 | B-3 | — | 0.79 | −1.8 | 2.68 | 0.05 | 6.8 | −1.6 | ○ |
| Example a26 | Z-26 | A-3 | 14 | B-1 | C-1 | 0.78 | −2.0 | 1.31 | 0.03 | 7.1 | −1.8 | ○ |
| Example a27 | Z-27 | A-3 | 14 | B-1 | C-1 | 0.79 | −1.9 | 1.26 | 0.03 | 7.0 | −1.9 | ○ |
| Example a28 | Z-28 | A-3 | 14 | B-1 | C-1 | 0.83 | −2.0 | 1.12 | 0.03 | 6.9 | −2.0 | ○ |

TABLE 3-continued

|  | Type of quaternary ammonium composition | Amount of (A) | | | | Pellet | | Molded piece | | | | |
|---|---|---|---|---|---|---|---|---|---|---|---|---|
|  | | Type of (A) | used (in terms of amount of nitrogen) [ppm] | Type of (B) | Type of (C) | FA [ppm] | Color tone | FA [ppm] | AA [ppm] | AL [ppb] | Color tone (b value) | Visual observation in MD |
| Example a29 | Z-29 | A-6 | 14 | B-1 | C-1 | 0.81 | −1.9 | 1.16 | 0.02 | 3.8 | −1.9 | ○ |
| Example a30 | Z-30 | A-8 | 14 | B-1 | C-1 | 0.79 | −2.0 | 0.97 | 0.02 | 3.5 | −2.0 | ○ |
| Example a31 | Z-31 | A-3 | 14 | B-1 | C-2 | 0.79 | −1.9 | 1.33 | 0.03 | 7.5 | −1.9 | ○ |
| Example a32 | Z-32 | A-3 | 14 | B-1 | C-2 | 0.83 | −2.0 | 1.31 | 0.03 | 7.2 | −2.0 | ○ |
| Example a33 | Z-33 | A-3 | 14 | B-1 | C-2 | 0.79 | −1.9 | 1.18 | 0.03 | 6.7 | −1.9 | ○ |
| Example a34 | Z-34 | A-6 | 14 | B-1 | C-2 | 0.78 | −2.0 | 1.14 | 0.02 | 3.5 | −2.0 | ○ |
| Example a35 | Z-35 | A-8 | 14 | B-1 | C-2 | 0.85 | −1.9 | 0.94 | 0.02 | 3.9 | −1.9 | ○ |
| Example a36 | Z-36 | A-6 | 14 | B-1 | — | 0.72 | −1.9 | 1.28 | 0.02 | 4.7 | −1.9 | ○ |
| Example a37 | Z-1' | A-1 | 10 | — | — | 0.75 | −1.0 | 5.89 | 1.28 | 11.5 | −0.9 | Δ |
| Example a38 | Z-6' | A-6 | 14 | — | — | 0.74 | −1.1 | 6.18 | 2.29 | 10.6 | −0.8 | Δ |
| Example a39 | Z-3' | A-3 | 14 | — | — | 0.74 | −1.1 | 5.91 | 2.38 | 12.1 | −0.8 | Δ |
| Example a40 | Z-36' | A-6 | 14 | — | — | 0.73 | −1.9 | 1.31 | 0.02 | 4.8 | −1.6 | ○ |
| Comparative Example a1 | — | — | — | — | — | 5.98 | 0.2 | 3.2 | 26.7 | 6.2 | O.D | X |

As shown in Table 3, each polyacetal where generation of formaldehyde was suppressed both before and after heating and melting processing (pellet and molded piece) could be obtained and each one also excellent in color tone was obtained in Examples a1 to a36. Furthermore, it was confirmed that generation of acetaldehyde and acrolein from the molded piece was also suppressed.

It was presumed that the reason why the b value was slightly higher in Examples a10 and a11 was because R2 in the quaternary ammonium compound (A) used was long and therefore the quaternary ammonium compound (C) easily remained in the polyacetal resin composition even after a stabilization treatment and was colored in heating and melting.

It was considered that the reason why the amount of formaldehyde generated from the molded piece was larger in Examples a14 and a18 was because the amount of (poly)alkylene glycol (B) used was too large.

It was presumed that the reason why the amount of formaldehyde generated from the molded piece was slightly larger in Examples a21 to a25 was because the molecular weight of polyalkylene glycol was high (p was large).

As shown in Table 3, when no quaternary ammonium compound (A) was used in Comparative Example a1, formaldehyde was considerably generated and no objective polyacetal in terms of the color tone and others could be obtained.

In Examples a37 to a39, while generation of formaldehyde from the pellet was suppressed, no (poly)alkylene glycol was used and thereby the amount of formaldehyde generated from the molded piece was increased. The color tone was also deteriorated. It was presumed that the quaternary ammonium compound (A) was degraded for some reason during storage for 6 months in the case where no (poly)alkylene glycol was used.

Example b

1. Method for Producing Crude Polyacetal

The temperature of a twin-paddle type continuous polymerization reactor equipped with a jacket capable of allowing a heat medium to pass (manufactured by KURIMOTO, LTD., diameter: 2B (2 inches), L (the distance from the raw material feed port to the discharge port of the polymerization reactor)/D (the inner diameter of the polymerization reactor)= 14.8) was adjusted to 80° C.

Next, boron trifluoride-di-n-butyl etherate as a polymerization catalyst at 0.20 g/hr, methylal as a low-molecular weight acetal at 1.53 g/hr, cyclohexane at 6.50 g/hr, and 1,3-dioxolane at 120.9 g/hr and trioxane at 3500 g/hr as a cyclic ether and/or a cyclic formal were continuously fed to the polymerization reactor through a pipe to perform polymerization, thereby providing crude polyacetal copolymer (bP-1).

Crude polyacetal copolymer (bP-1) was charged in an aqueous 0.1% by mass triethylamine solution, and the catalyst was deactivated. Thereafter, the resultant was dried at 120° C. after filtration/washing, thereby providing crude polyacetal copolymer (bP-2).

2. Examples/Comparative Examples

Examples b1 to b29

Crude polyacetal copolymer (bP-1) was charged in an aqueous 0.5% triethylamine solution, and the polymerization catalyst was deactivated. Thereafter, filtration and washing were performed, a solution of the quaternary ammonium compound (A) produced in each of Production Examples was added in an amount based on 100 parts by mass of crude polyacetal copolymer (bP-1) so that the concentration n of nitrogen was as shown in Table 4, and the resultant was uniformly mixed and then dried at 130° C.

Added was 0.2 parts by mass of 2,2'-methylenebis-(4-methyl-t-butylphenol) as an antioxidant based on 100 parts by mass of the crude polyacetal copolymer composition containing the quaternary ammonium compound (A) obtained, and fed to a twin-screw type extruder equipped with a vent.

Water was, if necessary, added to the crude polyacetal copolymer composition molten in the extruder, and an unstable terminal portion of the crude polyacetal copolymer was decomposed at a preset temperature of the extruder, of 210° C., for a retention time in the extruder, of 5 minutes. The polyacetal copolymer from which an unstable terminal portion was decomposed was subjected to degassing under a condition of a vent vacuum degree of 20 Torr, and extruded as a strand from a die section of the extruder, and pelletized.

The type of the quaternary ammonium compound (A) used, and the amount (content) of the quaternary ammonium compound (A) used based on the total mass of the polyacetal copolymer and the quaternary ammonium compound (A) (the concentration n of nitrogen derived from the quaternary ammonium compound (A)), the amounts of water and triethylamine added into the extruder, based on 100 parts by mass of the crude polyacetal copolymer composition, the amounts of formaldehyde (FA), acetaldehyde (AA) and acrolein (AL) generated from the pellet (from 1-b), and the amounts of formaldehyde (FA), acetaldehyde (AA) and acrolein (AL) generated from the molded article (from 2-b), as well as the color tone of the pellet and the color tone of the molded article (from 2-b) are collectively shown in Table 4.

Comparative Examples b1 to b3

The same manner as in Example b16 was performed except that no quaternary ammonium compound (A) was used and the amount of (C) used was changed. The results are collectively shown in Table 5.

Comparative Examples b4 and b5

The same manner as in Example b17 was performed except that no quaternary ammonium compound (A) was used and the amount of (C) used was changed. The results are collectively shown in Table 5.

Comparative Example b6

The same manner as in Example b1 was performed except that no quaternary ammonium compound (A) was used and the amount of water/triethylamine added was changed. The results are collectively shown in Table 5

Comparative Example b7

The same manner as in Example b1 was performed except that tetrakis[(2-hydroxyethyl)trimethylammonium] salt (D-1) of ethylenediaminetetraacetic acid was used instead of the quaternary ammonium compound (A), and the amount of water/triethylamine added was changed. The results are collectively shown in Table 5

Comparative Example b8

The same manner as in Comparative Example b7 was performed except that (2-hydroxyethyl) trimethylammonium salt (D-2) of polyacrylic acid (equivalent molar salt of an acrylic acid unit, number average molecular weight of polyacrylic acid=7000) was used instead of tetrakis[(2-hydroxyethyl)trimethylammonium] salt (D-1) of ethylenediaminetetraacetic acid. The results are collectively shown in Table 5

TABLE 4

| | Type of (A) | Amount of (A) used (in terms of amount of nitrogen) | Type of (C) | Amount of (C) used (in terms of amount of nitrogen) [ppm] | Amount of water/ triethylamine added (% by mass) | Pellet | | | Molded piece | | | Color tone (b value) |
|---|---|---|---|---|---|---|---|---|---|---|---|---|
| | | | | | | FA [ppm] | AA [ppm] | AL [ppb] | FA [ppm] | AA [ppm] | AL [ppb] | |
| Example b1 | A-1 | 8 | — | — | 2/0 | 0.76 | 0.01 | 1.2 | 1.49 | 0.02 | 6.2 | −2.0 |
| Example b2 | A-1 | 18 | — | — | 2/0 | 0.75 | 0.01 | 1.2 | 1.48 | 0.02 | 6.2 | −2.0 |
| Example b3 | A-1 | 25 | — | — | 2/0 | 0.74 | 0.04 | 1.2 | 3.47 | 1.01 | 6.2 | −1.7 |
| Example b4 | A-1 | 55 | — | — | 2/0 | 1.16 | 0.09 | 1.3 | 4.95 | 1.21 | 6.9 | −1.4 |
| Example b5 | A-2 | 8 | — | — | 2/0 | 0.76 | 0.02 | 1.3 | 1.54 | 0.02 | 7.7 | −1.9 |
| Example b6 | A-2 | 18 | — | — | 2/0 | 0.74 | 0.02 | 1.2 | 1.53 | 0.03 | 7.9 | −1.9 |
| Example b7 | A-3 | 4 | — | — | 2/0 | 0.78 | 0.02 | 1.1 | 2.23 | 0.02 | 9.1 | −2.0 |
| Example b8 | A-4 | 2 | — | — | 2/0 | 0.73 | 0.01 | 1 | 1.89 | 0.03 | 8.5 | −1.9 |
| Example b9 | A-5 | 15 | — | — | 2/0 | 0.64 | 0.02 | 1 | 1.18 | 0.02 | 8.6 | −1.9 |
| Example b10 | A-6 | 3 | — | — | 2/0 | 0.75 | 0.02 | 1.4 | 1.48 | 0.02 | 6.0 | −2.0 |
| Example b11 | A-7 | 19 | — | — | 2/0 | 0.80 | 0.01 | 1.3 | 1.04 | 0.02 | 3.9 | −1.7 |
| Example b12 | A-8 | 13 | — | — | 2/0 | 0.80 | 0.01 | 0.9 | 0.93 | 0.02 | 3.9 | −1.8 |
| Example b13 | A-9 | 0.8 | — | — | 2/0 | 0.92 | 0.03 | 1.1 | 1.92 | 0.05 | 5.5 | −1.8 |
| Example b14 | A-10 | 8 | — | — | 2/0 | 0.85 | 0.02 | 1.2 | 1.71 | 0.03 | 7.1 | −1.4 |
| Example b15 | A-11 | 4 | — | — | 2/0 | 0.93 | 0.02 | 1.2 | 1.98 | 0.06 | 7.7 | −1.3 |
| Example b16 | A-1 | 5 | C-1 | 5 | 2/0 | 0.67 | 0.01 | 1.0 | 0.98 | 0.02 | 4.8 | −2.0 |
| Example b17 | A-3 | 3 | C-2 | 7 | 2/0 | 0.60 | 0.02 | 1.0 | 1.63 | 0.02 | 6.8 | −2.0 |
| Example b18 | A-5 | 7 | C-1 | 3 | 2/0 | 0.65 | 0.01 | 0.9 | 1.15 | 0.02 | 7.1 | −2.0 |
| Example b19 | A-8 | 3 | C-1 | 7 | 2/0 | 0.59 | 0.02 | 1.0 | 1.31 | 0.02 | 3.5 | −2.0 |
| Example b20 | A-10 | 7 | C-1 | 3 | 2/0 | 0.68 | 0.01 | 1.0 | 1.16 | 0.02 | 7.5 | −1.3 |
| Example b21 | A-12 | 25 | — | — | 2/0 | 0.74 | 0.04 | 1.2 | 3.47 | 1.01 | 6.2 | −2.0 |
| Example b22 | A-13 | 25 | — | — | 2/0 | 0.73 | 0.05 | 1.2 | 3.46 | 1.04 | 6.0 | −2.0 |
| Example b23 | A-14 | 25 | — | — | 2/0 | 0.71 | 0.04 | 1.2 | 3.47 | 1.03 | 6.3 | −2.0 |
| Example b24 | A-15 | 25 | — | — | 2/0 | 0.74 | 0.06 | 1.2 | 3.44 | 1.01 | 6.2 | −2.0 |
| Example b25 | A-16 | 25 | — | — | 2/0 | 0.75 | 0.07 | 1.2 | 3.51 | 1.02 | 6.1 | −2.0 |
| Example b26 | A-17 | 25 | — | — | 2/0 | 0.74 | 0.04 | 1.2 | 3.5 | 1.01 | 6.2 | −2.0 |
| Example b27 | A-18 | 19 | — | — | 2/0 | 0.79 | 0.01 | 1.3 | 1.04 | 0.02 | 3.6 | −2.0 |
| Example b28 | A-19 | 13 | — | — | 2/0 | 0.80 | 0.01 | 1.0 | 0.91 | 0.02 | 3.5 | −2.0 |
| Example b29 | A-20 | 25 | — | — | 2/0 | 0.73 | 0.04 | 1.2 | 3.51 | 1.03 | 6.4 | −1.6 |

TABLE 5

| | Type of (A) | Amount of (A) used (in terms of amount of nitrogen) [ppm] | Type of (C) | Amount of (C) used (in terms of amount of nitrogen) [ppm] | Type of (D) | Amount of (D) used (in terms of amount of nitrogen) [ppm] | Amount of water/ triethylamine added (% by mass) |
|---|---|---|---|---|---|---|---|
| Comparative Example b1 | — | — | C-1 | 10 | — | — | 2/0 |
| Comparative Example b2 | — | — | C-1 | 5 | — | — | 2/0 |
| Comparative Example b3 | — | — | C-1 | 0.5 | — | — | 2/0 |
| Comparative Example b4 | — | — | C-2 | 10 | — | — | 2/0 |
| Comparative Example b5 | — | — | C-2 | 5 | — | — | 2/0 |
| Comparative Example b6 | | | | | | | 2/3 |
| Comparative Example b7 | — | — | — | — | D-1 | 10 | 3/0 |
| Comparative Example b8 | — | — | — | — | D-2 | 10 | 3/0 |

| | Pellet | | | Molded piece | | | Color |
|---|---|---|---|---|---|---|---|
| | FA [ppm] | AA [ppm] | AL [ppb] | FA [ppm] | AA [ppm] | AL [ppb] | tone (b value) |
| Comparative Example b1 | 0.77 | 0.01 | 1.1 | 1.27 | 0.09 | 19.4 | −1.8 |
| Comparative Example b2 | 0.99 | 0.02 | 1.2 | 1.44 | 0.22 | O.D | −1.8 |
| Comparative Example b3 | 1.68 | 0.03 | 1.5 | 1.55 | 0.53 | O.D | −1.8 |
| Comparative Example b4 | 0.89 | 0.02 | 1.1 | 1.35 | 0.16 | O.D | −1.8 |
| Comparative Example b5 | 1.16 | 0.02 | 1.6 | 1.51 | 0.18 | O.D | −1.8 |
| Comparative Example b6 | 5.27 | 0.12 | 3.2 | 25.3 | 6.2 | O.D | −1.9 |
| Comparative Example b7 | 3.21 | 0.44 | 1.1 | 4.8 | 0.84 | O.D | −1.2 |
| Comparative Example b8 | 3.38 | 0.42 | 1.8 | 5.1 | 0.93 | O.D | −1.2 |

As shown in Table 4, each polyacetal where generation of formaldehyde, acetaldehyde and acrolein was suppressed both before and after heating and melting processing (pellet and molded piece) could be obtained and each one also excellent in color tone was obtained in Examples b1 to b28.

Each polyacetal resin composition where, while the b value was slightly higher, generation of formaldehyde, acetaldehyde and acrolein was suppressed was obtained in Examples b4, b14, b15 and b20. It was presumed that the reason why the b value was slightly higher in Example b4 was because the amount of the quaternary ammonium compound (A) used was large, and it was also presumed that the reason why the b value was slightly higher in Examples b14, b15 and b20 was because R2 in the quaternary ammonium compound (A) used was long and therefore the quaternary ammonium compound (C) easily remained in the polyacetal resin composition even after a stabilization treatment and was colored in heating and melting.

Each polyacetal more excellent in color tone was obtained in Examples b21 to b28 where magnesium, calcium or sodium was allowed to coexist with the quaternary ammonium compound (A). On the contrary, a slight reduction in color tone was observed after heating and melting processing in Example b29 where potassium was allowed to coexist with the quaternary ammonium compound (A).

As shown in Table 5, while each polyacetal pellet where generation of formaldehyde, acetaldehyde and acrolein was suppressed could be obtained, generation of formaldehyde, acetaldehyde and acrolein in heating and melting could not be sufficiently suppressed, in Comparative Examples b1 to b5 where no quaternary ammonium compound (A) was used and only the quaternary ammonium compound (C) was used.

Even a polyacetal where generation of formaldehyde, acetaldehyde and acrolein was suppressed could not be obtained in Comparative Example b6 where no quaternary ammonium compound was used at all.

Generation of formaldehyde, acetaldehyde and acrolein could not be sufficiently suppressed in Comparative Examples b7 and b8 where quaternary ammonium compounds (D-1) and (D-2) including a nitrogen atom in a group corresponding to X in the formula (1) were used, respectively, instead of the quaternary ammonium compound (A).

Example c

1. Method for Producing Crude Polyacetal

The temperature of a twin-paddle type continuous polymerization reactor equipped with a jacket capable of allowing a heat medium to pass (manufactured by KURIMOTO, LTD., diameter: 2B (2 inches), L (the distance from the raw material feed port to the discharge port of the polymerization reactor)/D (the inner diameter of the polymerization reactor)= 14.8) was adjusted to 80° C.

Organic solvent-mixed solution (I) in which an organic solvent made of cyclohexane/heptane at a mass ratio of 9/1 and Irganox 1010 as an antioxidant were mixed at a mass ratio, organic solvent:antioxidant, of 980:1, was prepared.

Next, boron trifluoride-di-n-butyl etherate as a polymerization catalyst at 0.19 g/hr, methylal as a low-molecular weight acetal at 2.66 g/hr, organic solvent-mixed solution (I) above at 6.50 g/hr, and 1,3-dioxolane as a cyclic ether and/or a cyclic formal at 120.9 g/hr were continuously mixed at a temperature of 45° C. for a mixing time of 2 minutes, thereby providing pre-mixed liquid (I).

Pre-mixed liquid (I) at 130.25 g/hr was continuously fed to the polymerization reactor through a pipe, and trioxane at 3500 g/hr was continuously fed to the polymerization reactor through a pipe, for polymerization, thereby crude polyacetal copolymer (cP-1).

Crude polyacetal copolymer (cP-1) was charged in an aqueous 0.1% by mass triethylamine solution, and the catalyst was deactivated. Thereafter, the resultant was dried at 120° C. after filtration/washing, thereby providing crude polyacetal copolymer (cP-2).

2. Examples/Comparative Examples

Examples c1 to c44

Crude polyacetal copolymer (cP-1) was charged in an aqueous 0.1% triethylamine solution, and the polymerization catalyst was deactivated. Thereafter, filtration and washing were performed, a solution of the quaternary ammonium compound (A) produced in each of Production Examples was added in an amount based on 100 parts by mass of crude polyacetal copolymer (cP-1) so that the concentration n of nitrogen was as shown in Table 1, and the resultant was uniformly mixed and then dried at 120° C.

Added was 0.3 parts by mass of 2,2'-methylenebis-(4-methyl-t-butylphenol) as an antioxidant based on 100 parts by mass of the crude polyacetal copolymer composition containing the quaternary ammonium compound (A) obtained, and fed to a twin-screw type extruder equipped with a vent.

Water and/or triethylamine were/was, if necessary, added to the crude polyacetal copolymer composition molten in the extruder, and an unstable terminal portion of the crude polyacetal copolymer was decomposed at a preset temperature of the extruder, of 200° C., for a retention time in the extruder, of 5 minutes. The polyacetal copolymer composition from which an unstable terminal portion was decomposed was subjected to degassing under a condition of a vent vacuum degree of 20 Torr, and extruded as a strand from a die section of the extruder, and pelletized.

The type of the quaternary ammonium compound (A) used, and the amount (content) of the quaternary ammonium compound (A) used based on the total mass of the polyacetal copolymer and the quaternary ammonium compound (A) (the concentration n of nitrogen derived from the quaternary ammonium compound (A)), the amounts of water and triethylamine added into the extruder, based on 100 parts by mass of the crude polyacetal copolymer composition, the amounts of formaldehyde (FA), acetaldehyde (AA) and acrolein (AL) generated from the pellet (from 1-b), and the amounts of formaldehyde (FA), acetaldehyde (AA) and acrolein (AL) generated from the molded piece (from 2-b), as well as the color tone of the pellet and the color tone of the molded piece (from 2-b) are collectively shown in Table 6.

Examples c45 to c50

Crude polyacetal copolymer (cP-1) was charged in an aqueous 0.1% by mass triethylamine solution, and the polymerization catalyst was deactivated. Thereafter, filtration and washing were performed, a solution of the quaternary ammonium compound (A) produced in each of Production Examples, and the above-mentioned quaternary ammonium compound (C) were added in amounts based on 100 parts by mass of crude polyacetal copolymer (cP-1) so that the concentration n''' of nitrogen derived therefrom was as shown in Table 6, and the resultant was uniformly mixed and then dried at 120° C.

Added was 0.3 parts by mass of 2,2'-methylenebis-(4-methyl-t-butylphenol) as an antioxidant based on 100 parts by mass of the crude polyacetal copolymer composition containing the quaternary ammonium compounds (A) and (C) obtained, and fed to a twin-screw type extruder equipped with a vent.

Water and/or triethylamine were/was, if necessary, added to the crude polyacetal copolymer composition molten in the extruder, and an unstable terminal portion of the crude polyacetal copolymer was decomposed at a preset temperature of the extruder, of 200° C., for a retention time in the extruder, of 5 minutes. The polyacetal copolymer composition from which an unstable terminal portion was decomposed was subjected to degassing under a condition of a vent vacuum degree of 20 Torr, and extruded as a strand from a die section of the extruder, and pelletized.

The types of the quaternary ammonium compound (A) and the quaternary ammonium compound (C) used, and the amount (content) of each quaternary ammonium compound used (concentrations n and n''' of nitrogen) based on the total mass of the polyacetal copolymer and the quaternary ammonium compounds (A) and (C), the amounts of water and triethylamine added into the extruder, based on 100 parts by mass of the crude polyacetal copolymer composition, the amounts of formaldehyde (FA), acetaldehyde (AA) and acrolein (AL) generated from the pellet (from 1-b), and the amounts of formaldehyde (FA), acetaldehyde (AA) and acrolein (AL) generated from the molded piece (from 2-b), as well as the color tone of the pellet and the color tone of the molded piece (from 2-b) are collectively shown in Table 7.

Comparative Examples c1 to c9

The same manner as in Examples c1 to c44 was performed except that the quaternary ammonium compound (C) was used instead of the quaternary ammonium compound (A) in Examples c1 to c44. The results are collectively shown in Table 8.

Examples c51 to c65

Added was 0.3 parts by mass of 2,2'-methylenebis-(4-methyl-t-butylphenol) as an antioxidant based on 100 parts by mass of crude polyacetal copolymer (cP-2), and fed to a twin-screw type extruder equipped with a vent.

The quaternary ammonium compound (A) was added, together with water and/or triethylamine, to the crude polyacetal copolymer composition molten in the extruder in amounts so that the concentration n of nitrogen was as shown in Table 6, and an unstable terminal portion of the crude polyacetal copolymer was decomposed at a preset temperature of the extruder, of 200° C., for a retention time in the extruder, of 5 minutes. The polyacetal copolymer composition from which an unstable terminal portion was decomposed was subjected to degassing under a condition of a vent vacuum degree of 20 Torr, and extruded as a strand from a die section of the extruder, and pelletized.

The type of the quaternary ammonium compound (A) used, and the amount (concentration n of nitrogen) thereof used based on the total mass of the polyacetal copolymer and the quaternary ammonium compound, the amounts of water and triethylamine added into the extruder, based on 100 parts by mass of the crude polyacetal copolymer composition, the amounts of formaldehyde (FA), acetaldehyde (AA) and acrolein (AL) generated from the pellet (from 1-b), the amounts of formaldehyde (FA), acetaldehyde (AA) and acrolein (AL) generated from the molded piece (from 2-b), as well as the color tone of the pellet and the color tone of the molded piece (from 2-b) are collectively shown in Table 7.

Comparative Examples c10 to c15

The same manner as in Examples c51 to c65 was performed except that the quaternary ammonium compound (C) was used instead of the quaternary ammonium compound (A) in Examples c51 to c65. The results are collectively shown in Table 8.

Comparative Example c17

The same manner as in Examples c1 to c44 was performed except that tetrakis[(2-hydroxyethyl)trimethylammonium] salt (D-1) of ethylenediaminetetraacetic acid was used instead of the quaternary ammonium compound (A). The results are collectively shown in Table 8

Comparative Example c18

Added was 0.3 parts by mass of 2,2'-methylenebis-(4-methyl-t-butylphenol) as an antioxidant based on 100 parts by mass of crude polyacetal copolymer (cP-2), and fed to a twin-screw type extruder equipped with a vent.

(2-Hydroxyethyl)trimethylammonium salt (D-2) of polyacrylic acid (equivalent molar salt of an acrylic acid unit, number average molecular weight of polyacrylic acid=7000) was added, together with water and/or triethylamine, to the crude polyacetal copolymer composition molten in the extruder in amounts so that the concentration of nitrogen was as shown in Table 6, and an unstable terminal portion was decomposed at a preset temperature of the extruder, of 200° C., for a retention time in the extruder, of 5 minutes. The polyacetal copolymer composition from which an unstable terminal portion was decomposed was subjected to degassing under a condition of a vent vacuum degree of 20 Torr, and extruded as a strand from a die section of the extruder, and pelletized. The evaluation results of the pellet are shown in Table 8.

TABLE 6

| | Type of (A) | Amount of (A) used (in terms of amount of nitrogen) [ppm] | Amount of (C) used (in terms of amount of nitrogen) [ppm] | Amount of (D) used (in terms of amount of nitrogen) [ppm] | Amount of water/ triethylamine added (% by mass) | Pellet FA [ppm] | AA [ppm] |
|---|---|---|---|---|---|---|---|
| Example c1 | A-1 | 10 | — | — | 3/0 | 0.76 | 0.01 |
| Example c2 | A-1 | 1 | — | — | 3/0 | 0.88 | 0.02 |
| Example c3 | A-1 | 0.5 | — | — | 3/0 | 1.08 | 0.02 |
| Example c4 | A-1 | 10 | — | — | 2/0.3 | 0.77 | 0.01 |
| Example c5 | A-2 | 10 | — | — | 3/0 | 0.74 | 0.02 |
| Example c6 | A-2 | 1 | — | — | 3/0 | 0.91 | 0.03 |
| Example c7 | A-2 | 0.5 | — | — | 3/0 | 1.15 | 0.04 |
| Example c8 | A-2 | 10 | — | — | 2/0.3 | 0.68 | 0.02 |
| Example c9 | A-3 | 10 | — | — | 3/0 | 0.68 | 0.01 |
| Example c10 | A-3 | 1 | — | — | 3/0 | 0.88 | 0.02 |
| Example c11 | A-3 | 0.5 | — | — | 3/0 | 1.11 | 0.02 |
| Example c12 | A-3 | 10 | — | — | 2/0.3 | 0.64 | 0.01 |
| Example c13 | A-4 | 10 | — | — | 3/0 | 0.66 | 0.01 |
| Example c14 | A-4 | 1 | — | — | 3/0 | 0.75 | 0.02 |
| Example c15 | A-4 | 0.5 | — | — | 3/0 | 0.99 | 0.02 |
| Example c16 | A-4 | 10 | — | — | 2/0.3 | 0.64 | 0.01 |
| Example c17 | A-5 | 10 | — | — | 3/0 | 0.65 | 0.02 |
| Example c18 | A-5 | 1 | — | — | 3/0 | 0.79 | 0.03 |
| Example c19 | A-5 | 0.5 | — | — | 3/0 | 0.87 | 0.04 |
| Example c20 | A-5 | 10 | — | — | 2/0.3 | 0.65 | 0.02 |
| Example c21 | A-6 | 10 | — | — | 3/0 | 0.71 | 0.01 |
| Example c22 | A-6 | 1 | — | — | 3/0 | 0.78 | 0.02 |
| Example c23 | A-6 | 0.5 | — | — | 3/0 | 0.87 | 0.02 |
| Example c24 | A-6 | 10 | — | — | 2/0.3 | 0.77 | 0.01 |
| Example c25 | A-7 | 10 | — | — | 3/0 | 0.81 | 0.01 |
| Example c26 | A-7 | 1 | — | — | 3/0 | 0.98 | 0.02 |
| Example c27 | A-7 | 0.5 | — | — | 3/0 | 1.31 | 0.02 |
| Example c28 | A-7 | 10 | — | — | 2/0.3 | 0.84 | 0.01 |
| Example c29 | A-8 | 10 | — | — | 3/0 | 0.81 | 0.01 |
| Example c30 | A-8 | 1 | — | — | 3/0 | 0.99 | 0.02 |
| Example c31 | A-8 | 0.5 | — | — | 3/0 | 1.13 | 0.02 |
| Example c32 | A-8 | 10 | — | — | 2/0.3 | 0.74 | 0.01 |
| Example c33 | A-9 | 10 | — | — | 3/0 | 0.68 | 0.01 |
| Example c34 | A-9 | 1 | — | — | 3/0 | 0.91 | 0.02 |
| Example c35 | A-9 | 0.5 | — | — | 3/0 | 1.06 | 0.02 |
| Example c36 | A-9 | 10 | — | — | 2/0.3 | 0.7 | 0.01 |

TABLE 6-continued

| | | | | | | | |
|---|---|---|---|---|---|---|---|
| Example c37 | A-10 | 10 | — | — | 3/0 | 0.81 | 0.01 |
| Example c38 | A-10 | 5 | — | — | 3/0 | 0.89 | 0.02 |
| Example c39 | A-10 | 0.5 | — | — | 3/0 | 1.51 | 0.02 |
| Example c40 | A-10 | 20 | — | — | 2/0.3 | 0.79 | 0.01 |
| Example c41 | A-11 | 10 | — | — | 3/0 | 0.82 | 0.01 |
| Example c42 | A-11 | 5 | — | — | 3/0 | 0.92 | 0.02 |
| Example c43 | A-11 | 0.5 | — | — | 3/0 | 1.46 | 0.02 |
| Example c44 | A-11 | 20 | — | — | 2/0.3 | 0.81 | 0.01 |

| | Pellet | | Molded piece | | | |
|---|---|---|---|---|---|---|
| | AL [ppb] | Nitrogen content [ppm] | FA [ppm] | AA [ppm] | AL [ppb] | Color tone (b value) |
| Example c1 | 1.2 | 2.6 | 1.49 | 0.02 | 6.2 | −2.0 |
| Example c2 | 1.3 | 0.39 | 2.95 | 0.03 | 6.9 | −2.0 |
| Example c3 | 1.6 | 0.08 | 4.38 | 0.04 | 12.9 | −2.0 |
| Example c4 | 1.3 | 2.7 | 2.08 | 0.02 | 5.1 | −2.0 |
| Example c5 | 1.3 | 3.2 | 1.59 | 0.02 | 7.9 | −1.9 |
| Example c6 | 1.2 | 0.65 | 2.71 | 0.03 | 10.4 | −1.9 |
| Example c7 | 1.6 | 0.12 | 4.08 | 0.04 | 16.8 | −1.9 |
| Example c8 | 1 | 3.3 | 2.30 | 0.02 | 7.8 | −1.9 |
| Example c9 | 1 | 2.8 | 1.64 | 0.02 | 8.6 | −2.0 |
| Example c10 | 1.3 | 0.58 | 2.63 | 0.03 | 15.8 | −2.0 |
| Example c11 | 1.8 | 0.11 | 4.11 | 0.04 | 18.5 | −2.0 |
| Example c12 | 1 | 2.8 | 2.01 | 0.02 | 8.2 | −2.0 |
| Example c13 | 1 | 3.4 | 1.31 | 0.02 | 6.2 | −1.8 |
| Example c14 | 1 | 0.68 | 1.96 | 0.03 | 8.9 | −1.8 |
| Example c15 | 1.1 | 0.05 | 3.65 | 0.04 | 15.9 | −1.8 |
| Example c16 | 1.1 | 3.4 | 1.44 | 0.02 | 6.1 | −1.8 |
| Example c17 | 1.1 | 2.9 | 1.18 | 0.02 | 8.8 | −2.0 |
| Example c18 | 1.2 | 0.42 | 1.54 | 0.03 | 11.4 | −2.0 |
| Example c19 | 1.8 | 0.11 | 3.46 | 0.04 | 12.6 | −2.0 |
| Example c20 | 1.6 | 2.8 | 0.35 | 0.02 | 8.8 | −2.0 |
| Example c21 | 1.1 | 1.6 | 1.18 | 0.02 | 4.8 | −2.0 |
| Example c22 | 1.6 | 0.19 | 1.54 | 0.03 | 6.3 | −2.0 |
| Example c23 | 1.6 | 0.01 | 3.46 | 0.04 | 8.2 | −2.0 |
| Example c24 | 1.2 | 1.9 | 1.35 | 0.02 | 4.1 | −2.0 |
| Example c25 | 1.3 | 2.2 | 1.09 | 0.02 | 3.7 | −1.9 |
| Example c26 | 1.8 | 0.35 | 1.66 | 0.03 | 6.0 | −1.9 |
| Example c27 | 1.9 | 0.01 | 3.02 | 0.04 | 7.7 | −1.9 |
| Example c28 | 1.1 | 2.3 | 0.98 | 0.02 | 4.2 | −1.9 |
| Example c29 | 0.9 | 1.8 | 0.95 | 0.02 | 3.9 | −2.0 |
| Example c30 | 1.1 | 0.28 | 1.56 | 0.03 | 6.5 | −2.0 |
| Example c31 | 1.3 | 0.01 | 3.80 | 0.04 | 7.4 | −2.0 |
| Example c32 | 1.1 | 1.9 | 1.02 | 0.02 | 3.3 | −2.0 |
| Example c33 | 0.9 | 2.4 | 1.02 | 0.02 | 3.4 | −1.8 |
| Example c34 | 1.1 | 0.42 | 1.65 | 0.03 | 5.7 | −1.8 |
| Example c35 | 1.8 | 0.08 | 3.55 | 0.04 | 8.3 | −1.8 |
| Example c36 | 1 | 2.6 | 1.01 | 0.02 | 3.4 | −1.8 |
| Example c37 | 1.2 | 6.8 | 1.56 | 0.03 | 5.9 | −1.4 |
| Example c38 | 1.3 | 2.2 | 1.85 | 0.04 | 9.1 | −1.4 |
| Example c39 | 1.5 | 0.3 | 4.55 | 0.05 | 10.1 | −1.5 |
| Example c40 | 1.1 | 8.8 | 1.63 | 0.02 | 8.4 | −1.2 |
| Example c41 | 1.1 | 7.1 | 1.77 | 0.04 | 5.7 | −1.2 |
| Example c42 | 1.2 | 2.5 | 1.94 | 0.06 | 8.9 | −1.3 |
| Example c43 | 1.6 | 0.5 | 5.87 | 0.08 | 10.0 | −1.4 |
| Example c44 | 1.0 | 7.6 | 1.88 | 0.04 | 8.3 | −1.0 |

TABLE 7

| | Type of (A) | Amount of (A) used (in terms of amount of nitrogen) | Type of (C) | Amount of (C) used (in terms of amount of nitrogen) | Amount of (D) used (in terms of amount of nitrogen) | Amount of water/ triethylamine added (% by mass) | Pellet FA [ppm] | AA [ppm] |
|---|---|---|---|---|---|---|---|---|
| Example c45 | A-1 | 10 | C-1 | 5 | — | 3/0 | 0.68 | 0.01 |
| Example c46 | A-1 | 5 | C-1 | 10 | — | 3/0 | 0.59 | 0.01 |
| Example c47 | A-3 | 5 | C-1 | 5 | — | 2/0.3 | 0.61 | 0.02 |
| Example c48 | A-5 | 5 | C-1 | 5 | — | 2/0.3 | 0.68 | 0.01 |
| Example c49 | A-8 | 5 | C-1 | 5 | — | 2/0.3 | 0.54 | 0.01 |
| Example c50 | A-10 | 5 | C-1 | 5 | — | 3/0 | 0.69 | 0.01 |
| Example c51 | A-1 | 10 | — | — | — | 3/0 | 0.78 | 0.01 |
| Example c52 | A-1 | 5 | — | — | — | 3/0 | 0.74 | 0.01 |

TABLE 7-continued

| | | | | | | | | |
|---|---|---|---|---|---|---|---|---|
| Example c53 | A-1 | 5 | — | — | — | 2/0.3 | 0.78 | 0.01 |
| Example c54 | A-3 | 10 | — | — | — | 3/0 | 0.67 | 0.01 |
| Example c55 | A-3 | 5 | — | — | — | 3/0 | 0.69 | 0.01 |
| Example c56 | A-3 | 5 | — | — | — | 2/0.3 | 0.71 | 0.01 |
| Example c57 | A-6 | 10 | — | — | — | 3/0 | 0.7 | 0.01 |
| Example c58 | A-6 | 5 | — | — | — | 3/0 | 0.69 | 0.01 |
| Example c59 | A-6 | 5 | — | — | — | 2/0.3 | 0.69 | 0.01 |
| Example c60 | A-8 | 10 | — | — | — | 3/0 | 0.78 | 0.01 |
| Example c61 | A-8 | 5 | — | — | — | 3/0 | 0.76 | 0.01 |
| Example c62 | A-8 | 5 | — | — | — | 3/0 | 0.79 | 0.01 |
| Example c63 | A-9 | 10 | — | — | — | 3/0 | 0.71 | 0.01 |
| Example c64 | A-9 | 5 | — | — | — | 3/0 | 0.71 | 0.01 |
| Example c65 | A-9 | 10 | — | — | — | 2/0.3 | 0.69 | 0.01 |

| | Pellet | | Molded piece | | | |
|---|---|---|---|---|---|---|
| | AL [ppb] | Nitrogen content [ppm] | FA [ppm] | AA [ppm] | AL [ppb] | Color tone (b value) |
| Example c45 | 1.0 | 2.8 | 1.06 | 0.02 | 5.8 | −2.0 |
| Example c46 | 0.9 | 1.6 | 1.52 | 0.02 | 5.9 | −2.0 |
| Example c47 | 1.0 | 1.6 | 1.65 | 0.02 | 8.2 | −2.0 |
| Example c48 | 0.9 | 1.8 | 1.21 | 0.02 | 7.7 | −2.0 |
| Example c49 | 0.9 | 1.1 | 1.26 | 0.02 | 3.2 | −2.0 |
| Example c50 | 1.0 | 3.5 | 1.13 | 0.02 | 7.1 | −1.4 |
| Example c51 | 1.2 | 2.6 | 1.51 | 0.02 | 6.1 | −2.0 |
| Example c52 | 1.2 | 2.6 | 1.46 | 0.02 | 6.1 | −2.0 |
| Example c53 | 1.2 | 2.6 | 1.43 | 0.02 | 6.3 | −2.0 |
| Example c54 | 1 | 2.8 | 1.61 | 0.02 | 8.7 | −2.0 |
| Example c55 | 1 | 2.8 | 1.63 | 0.02 | 8.4 | −2.0 |
| Example c56 | 1 | 2.8 | 1.64 | 0.02 | 8.4 | −2.0 |
| Example c57 | 1.1 | 1.6 | 1.11 | 0.02 | 4.9 | −2.0 |
| Example c58 | 1.1 | 1.6 | 1.08 | 0.02 | 4.8 | −2.0 |
| Example c59 | 1.1 | 1.6 | 1.03 | 0.02 | 4.6 | −2.0 |
| Example c60 | 0.9 | 1.8 | 1.1 | 0.02 | 3.7 | −2.0 |
| Example c61 | 0.9 | 1.8 | 1.02 | 0.02 | 3.7 | −2.0 |
| Example c62 | 0.9 | 1.8 | 0.92 | 0.02 | 3.5 | −2.0 |
| Example c63 | 0.9 | 2.4 | 0.98 | 0.02 | 3.3 | −1.8 |
| Example c64 | 0.9 | 2.4 | 0.99 | 0.02 | 3.4 | −1.8 |
| Example c65 | 0.9 | 2.4 | 1.13 | 0.02 | 3.4 | −1.8 |

TABLE 8

| | Type of (A) | Amount of (A) used (in terms of amount of nitrogen) | Type of (C) | Amount of (C) used (in terms of amount of nitrogen) | Type of (D) | Amount of (D) used (in terms of amount of nitrogen) | Amount of water/ triethylamine added (% by mass) |
|---|---|---|---|---|---|---|---|
| Comparative Example c1 | — | — | C-1 | 10 | — | — | 3/0 |
| Comparative Example c2 | — | — | C-1 | 5 | — | — | 3/0 |
| Comparative Example c3 | — | — | C-1 | 0.5 | — | — | 3/0 |
| Comparative Example c4 | — | — | C-1 | 10 | — | — | 2/0.3 |
| Comparative Example c5 | — | — | C-2 | 10 | — | — | 3/0 |
| Comparative Example c6 | — | — | C-2 | 5 | — | — | 3/0 |
| Comparative Example c7 | — | — | C-2 | 0.5 | — | — | 3/0 |
| Comparative Example e8 | — | — | C-2 | 10 | — | — | 2/0.3 |
| Comparative Example c9 | — | — | — | — | — | — | 3/3 |
| Comparative Example c10 | — | — | C-1 | 10 | — | — | 3/0 |
| Comparative Example c11 | — | — | C-1 | 5 | — | — | 3/0 |
| Comparative Example c12 | — | — | C-1 | 10 | — | — | 2/0.3 |
| Comparative Example c13 | — | — | C-2 | 10 | — | — | 3/0 |

TABLE 8-continued

| | | | | | | | |
|---|---|---|---|---|---|---|---|
| Comparative Example c14 | — | — | C-2 | 5 | — | — | 3/0 |
| Comparative Example c15 | — | — | C-2 | 10 | — | — | 2/0.3 |
| Comparative Example c17 | — | — | — | — | D-1 | 10 | 3/0 |
| Comparative Example c18 | — | — | — | — | D-2 | 10 | 3/0 |

| | Pellet | | | | Molded piece | | | |
|---|---|---|---|---|---|---|---|---|
| | FA [ppm] | AA [ppm] | AL [ppb] | Nitrogen content [ppm] | FA [ppm] | AA [ppm] | AL [ppb] | Color tone (b value) |
| Comparative Example c1 | 0.78 | 0.01 | 1.1 | 0.54 | 1.25 | 0.09 | 19.6 | −1.8 |
| Comparative Example c2 | 0.98 | 0.02 | 1.2 | 0.22 | 1.42 | 0.21 | O.D | −1.8 |
| Comparative Example c3 | 1.61 | 0.03 | 1.5 | 0.01 | 1.53 | 0.45 | O.D | −1.8 |
| Comparative Example c4 | 0.71 | 0.01 | 1.1 | 0.65 | 1.21 | 0.11 | 18.8 | −1.8 |
| Comparative Example c5 | 0.91 | 0.02 | 1.2 | 0.42 | 1.36 | 0.15 | O.D | −1.8 |
| Comparative Example c6 | 1.16 | 0.02 | 1.6 | 0.18 | 1.51 | 0.18 | O.D | −1.8 |
| Comparative Example c7 | 1.34 | 0.02 | 1.6 | 0.01 | 1.56 | 0.62 | O.D | −1.8 |
| Comparative Example e8 | 0.88 | 0.02 | 1.1 | 0.38 | 1.31 | 0.14 | O.D | −1.8 |
| Comparative Example c9 | 5.27 | 0.12 | 3.2 | 0 | 25.3 | 6.2 | O.D | −1.9 |
| Comparative Example c10 | 0.77 | 0.01 | 1.2 | 0.55 | 1.19 | 0.21 | O.D | −1.8 |
| Comparative Example c11 | 0.98 | 0.02 | 1.2 | 0.23 | 1.38 | 0.12 | O.D | −1.8 |
| Comparative Example c12 | 0.72 | 0.01 | 1.1 | 0.66 | 1.21 | 0.13 | O.D | −1.8 |
| Comparative Example c13 | 0.93 | 0.02 | 1.2 | 0.42 | 1.36 | 0.16 | O.D | −1.8 |
| Comparative Example c14 | 1.15 | 0.02 | 1.6 | 0.20 | 1.58 | 0.19 | O.D | −1.8 |
| Comparative Example c15 | 0.87 | 0.02 | 1.2 | 0.37 | 1.42 | 0.13 | O.D | −1.8 |
| Comparative Example c17 | 3.21 | 0.44 | 1.1 | 9.5 | 4.8 | 0.84 | O.D | −1.2 |
| Comparative Example c18 | 3.38 | 0.42 | 1.8 | 9.6 | 5.1 | 0.93 | O.D | −1.2 |

As shown in Tables 6 and 7, each polyacetal resin composition where generation of formaldehyde, acetaldehyde and acrolein was suppressed both before and after heating and melting processing (pellet and molded piece) could be obtained and each one also excellent in color tone was obtained in Examples c1 to c65.

Each polyacetal resin composition where, while the b value was slightly higher, generation of formaldehyde, acetaldehyde and acrolein was suppressed was obtained in Examples c37 to c44, and c50. It was presumed that the reason why the b value was slightly higher in such Examples was because R2 in the quaternary ammonium compound (A) used was long and therefore the quaternary ammonium compound (A) easily remained in the polyacetal resin composition even after a stabilization treatment, and was colored in heating and melting.

While each polyacetal resin composition pellet where generation of formaldehyde, acetaldehyde and acrolein was suppressed could be obtained, generation of formaldehyde, acetaldehyde and acrolein in heating and melting could not be sufficiently suppressed, in Comparative Examples c1 to c8 and c10 to c15 where no quaternary ammonium compound (A) was used and only the quaternary ammonium compound (C) was used.

Even a polyacetal resin composition pellet where generation of formaldehyde, acetaldehyde and acrolein was suppressed could not be obtained in Comparative Example c9 where no quaternary ammonium compound was used at all.

Generation of formaldehyde, acetaldehyde and acrolein could not be sufficiently suppressed in Comparative Examples c17 and c18 where quaternary ammonium compound (D-1) including a nitrogen atom in a group corresponding to X in the formula (1) was used instead of the quaternary ammonium compound (A) and quaternary ammonium compound (D-2) including polycarboxylic acid in a group corresponding to X in the formula (1) was used instead of the quaternary ammonium compound (A), respectively.

INDUSTRIAL APPLICABILITY

The quaternary ammonium compound (A) can be used in various applications, and can be effectively used particularly for suppression of generation of a volatile organic compound from polyacetal.

The present application is based on Japanese Patent Applications (Japanese Patent Application No. 2016-

150397, Japanese Patent Application No. 2016-150950, and Japanese Patent Application No. 2017-114287) filed with JPO on Jul. 29, 2016, Aug. 1, 2016, and Jun. 9, 2017, respectively, the contents of which are herein incorporated by reference.

The invention claimed is:

1. A quaternary ammonium composition comprising:

a quaternary ammonium compound represented by the following formula (1):

$$[(R1)_m(R2)_{4-m}N^+]_n X^{n-} \quad (1)$$

wherein each R1 independently represents an unsubstituted alkyl group or substituted alkyl group having 1 to 30 carbon atoms; an aryl group having 6 to 20 carbon atoms; an aralkyl group where an unsubstituted alkyl group or substituted alkyl group having 1 to 30 carbon atoms is substituted with at least one aryl group having 6 to 20 carbon atoms; or an alkylaryl group where an aryl group having 6 to 20 carbon atoms is substituted with at least one unsubstituted alkyl group or substituted alkyl group having 1 to 30 carbon atoms; wherein the unsubstituted alkyl group and the substituted alkyl group are straight, branched, or cyclic; the substituent of the substituted alkyl group is halogen, a hydroxyl group, an aldehyde group, a carboxyl group, an amino group, or an amide group; and any hydrogen atom in the unsubstituted alkyl group, aryl group, aralkyl group, and alkylaryl group may be replaced by halogen;

each R2 independently represents a group having 2 to 6 carbon atoms and 2 to 3 oxygen atoms, the group represented by the following formula:

—(RO)k-H, wherein R represents a substituted or unsubstituted alkyl group and k represents a natural number of 2 or more;

m and n each represents an integer of 1 to 3; and

X represents an acid residue of at least one selected from the group consisting of formic acid, acetic acid, and propionic acid; and a (poly)alkylene glycol (B) represented by the following formula (2), and/or a quaternary ammonium compound (C) represented by the following formula (3):

$$R3-O-(C_2H_4O)_p-R4 \quad (2)$$

wherein R3 and R4 each independently represents a hydrogen atom; an unsubstituted alkyl group or substituted alkyl group having 1 to 30 carbon atoms; an aryl group having 6 to 20 carbon atoms; an aralkyl group where an unsubstituted alkyl group or substituted alkyl group having 1 to 30 carbon atoms is substituted with at least one aryl group having 6 to 20 carbon atoms; or an alkylaryl group where an aryl group having 6 to 20 carbon atoms is substituted with at least one unsubstituted alkyl group or substituted alkyl group having 1 to 30 carbon atoms; wherein the unsubstituted alkyl group or substituted alkyl group is straight, branched, or cyclic; the substituent of the substituted alkyl group is halogen, a hydroxyl group, an aldehyde group, a carboxyl group, an amino group, or an amide group; and any hydrogen atom in the unsubstituted alkyl group, aryl group, aralkyl group, and alkylaryl group may be replaced by halogen; and p represents a natural number;

$$[R5R6R7R8N^+]_l Y^{l-} \quad (3)$$

wherein R5, R6, R7, and R8 each independently represents an unsubstituted alkyl group or substituted alkyl group having 1 to 30 carbon atoms; an aryl group having 6 to 20 carbon atoms; an aralkyl group where an unsubstituted alkyl group or substituted alkyl group having 1 to 30 carbon atoms is substituted with at least one aryl group having 6 to 20 carbon atoms; or an alkylaryl group where an aryl group having 6 to 20 carbon atoms is substituted with at least one unsubstituted alkyl group or substituted alkyl group having 1 to 30 carbon atoms; wherein the unsubstituted alkyl group and the substituted alkyl group are straight, branched, or cyclic; the substituent of the substituted alkyl group is halogen, a hydroxyl group, an aldehyde group, a carboxyl group, an amino group, or an amide group; and any hydrogen atom in the unsubstituted alkyl group, aryl group, aralkyl group, and alkylaryl group may be replaced by halogen;

l represents an integer of 1 to 3; and

Y represents a hydroxyl group, or an acid residue of a compound selected from the group consisting of a carboxylic acid having 1 to 20 carbon atoms, a hydroacid, an oxo-acid, an inorganic thioacid, and an organic thioacid having 1 to 20 carbon atoms.

2. The quaternary ammonium composition according to claim 1, further comprising at least one metal atom selected from the group consisting of magnesium, sodium, and calcium.

3. An agent for suppression of generation of a volatile organic compound from polyacetal, the agent comprising the quaternary ammonium composition according to claim 1.

4. A polyacetal resin composition comprising:

polyacetal; and the agent for suppression of generation of a volatile organic compound from polyacetal according to claim 3.

5. The polyacetal resin composition according to claim 4, wherein a concentration n of nitrogen derived from the quaternary ammonium compound (A) represented by the formula (I), represented by the following expression, is 0.1 ppb or more and 30 ppm or less on a mass basis:

$$n = S6 \times 14/T \quad (I)$$

wherein S represents an amount of the quaternary ammonium compound (A) based on a total amount of polyacetal and the quaternary ammonium compound (A), 14 represents an atomic weight of nitrogen, and T represents a molecular weight of the quaternary ammonium compound (A).

6. A method for producing polyacetal, comprising:

a step of subjecting a polyacetal having a thermally unstable terminal portion to a heat treatment in the presence of the quaternary ammonium composition according to claim 1.

* * * * *

UNITED STATES PATENT AND TRADEMARK OFFICE
CERTIFICATE OF CORRECTION

PATENT NO.       : 10,815,190 B2
APPLICATION NO.  : 16/321211
DATED            : October 27, 2020
INVENTOR(S)      : Kondo Page 1 of 1

It is certified that error appears in the above-identified patent and that said Letters Patent is hereby corrected as shown below:

In the Claims

Column 56, Line 47 (Claim 5, Line 6) please change "$n=S6\times14/T$" to -- $n=S\times14/T$ --

Signed and Sealed this
Sixth Day of April, 2021

Drew Hirshfeld
*Performing the Functions and Duties of the*
*Under Secretary of Commerce for Intellectual Property and*
*Director of the United States Patent and Trademark Office*